United States Patent

Stanke et al.

[11] Patent Number: 5,996,415
[45] Date of Patent: Dec. 7, 1999

[54] APPARATUS AND METHOD FOR CHARACTERIZING SEMICONDUCTOR WAFERS DURING PROCESSING

[75] Inventors: Fred E. Stanke, Cupertino; Butrus T. Khuri-Yakub, Palo Alto; Hung Pham, San Jose; Talat Hasan, Saratoga, all of Calif.

[73] Assignee: Sensys Instruments Corporation, Sunnyvale, Calif.

[21] Appl. No.: 08/847,144

[22] Filed: Apr. 30, 1997

[51] Int. Cl.$^6$ .................................................. G01N 29/18
[52] U.S. Cl. .............................. 73/597; 73/644; 374/119; 374/137; 437/8; 437/9
[58] Field of Search .................. 73/597, 644, 643, 73/DIG. 1; 374/119, 137, 117; 437/8, 9, 225

[56] References Cited

U.S. PATENT DOCUMENTS

| | | | |
|---|---|---|---|
| 4,106,327 | 8/1978 | Adler et al. | 73/1 DV |
| 4,215,575 | 8/1980 | Akita et al. | 73/339 A |
| 4,513,384 | 4/1985 | Rosencwaig | 364/563 |
| 4,625,556 | 12/1986 | Sakahara et al. | 73/602 |
| 4,789,969 | 12/1988 | Naville | 367/36 |
| 4,803,884 | 2/1989 | Kaneta et al. | 73/598 |
| 4,899,589 | 2/1990 | Thompson et al. | 73/597 |
| 4,928,269 | 5/1990 | Kimball et al. | 367/35 |
| 5,159,838 | 11/1992 | Lynnworth | 73/644 |
| 5,216,638 | 6/1993 | Wright | 367/35 |
| 5,240,552 | 8/1993 | Yu et al. | 156/636 |
| 5,249,466 | 10/1993 | Jones | 73/633 |
| 5,271,274 | 12/1993 | Khuri-Yakab et al. | 73/597 |
| 5,286,313 | 2/1994 | Schultz et al. | 73/597 |
| 5,305,641 | 4/1994 | Kuramochi et al. | 73/598 |
| 5,438,872 | 8/1995 | Kobayashi et al. | 73/597 |
| 5,439,551 | 8/1995 | Meikle et al. | 156/626.1 |
| 5,469,742 | 11/1995 | Lee et al. | 73/567 |
| 5,546,811 | 8/1996 | Rogers et al. | 73/800 |
| 5,585,921 | 12/1996 | Pepper et al. | 356/357 |
| 5,604,592 | 2/1997 | Kotidis et al. | 356/357 |
| 5,607,236 | 3/1997 | Takagi et al. | 374/117 |
| 5,672,830 | 9/1997 | Rogers et al. | 73/597 |
| 5,723,791 | 3/1998 | Koch et al. | 73/597 |

*Primary Examiner*—Hezron Williams
*Assistant Examiner*—Rose M. Miller
*Attorney, Agent, or Firm*—Flehr Hohbach Test Albritton & Herbert LLP

[57] ABSTRACT

An apparatus and method are disclosed for characterizing semiconductor wafers or other test objects that can support acoustic waves. Source and receiving transducers are configured in various arrangements to respectively excite and detect acoustic waves (e.g., Lamb waves) in a wafer to be characterized. Signals representing the detected waves are digitally processed and used to compute a measurement set correlated with the waves' velocity in the wafer. A characterization sensitivity is provided that describes how different wafer characteristics of interest vary with changes in the propagation of the acoustic waves. Using the characterization sensitivity and measurement sets computed at a setup time when all wafer characteristics are known and one or more process times when at least one of the characteristics is not known the perturbation in wafer characteristics between the setup and the process times can be determined. Characterization accuracy is improved by a wafer calibration procedure wherein measurement offsets from known conditions are determined for each wafer being characterized. An apparatus and technique are disclosed for correcting for anisotropy of acoustic wave velocity due to the direction of wave propagation with respect to a preferred crystallographic axis of the wafer. An apparatus and technique are also described for measuring wafer temperature using a single transducer whose temperature is related to the temperature of the wafer and, optionally, resonator structures. For characterization steps that occur when the wafer is chucked, a chuck structure is described that reduces the likelihood of the chuck interfering with the waves in the wafer.

22 Claims, 22 Drawing Sheets

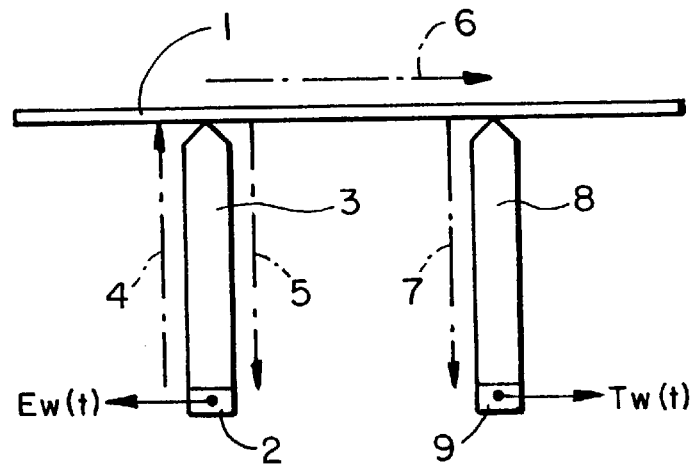
FIG_1
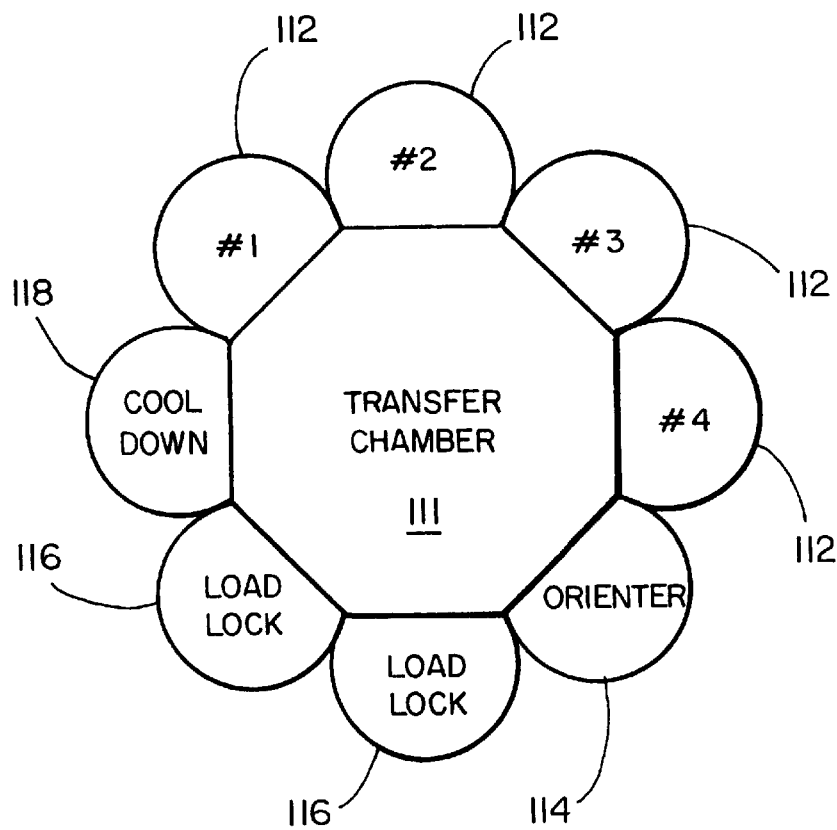
FIG_2

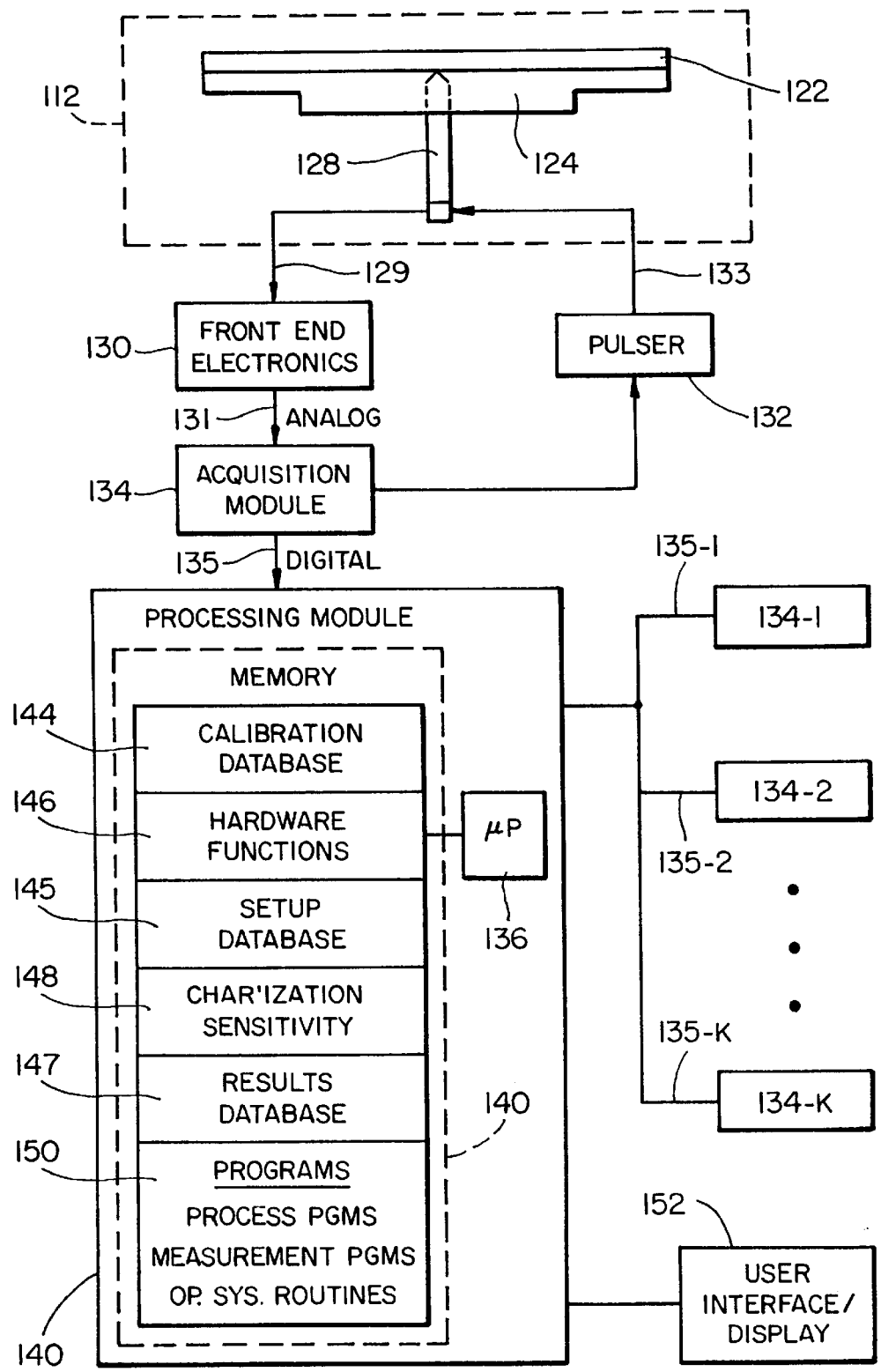
FIG_3A

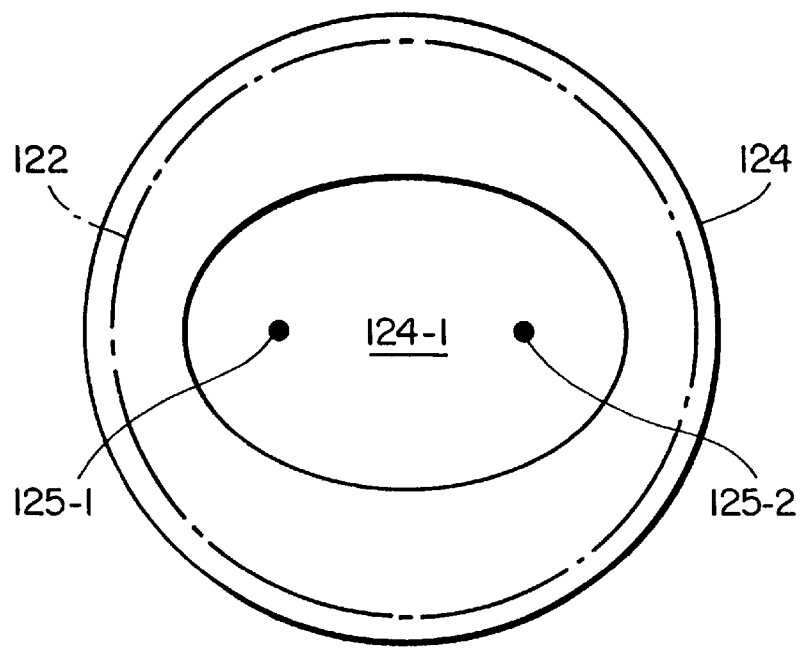
FIG_3B
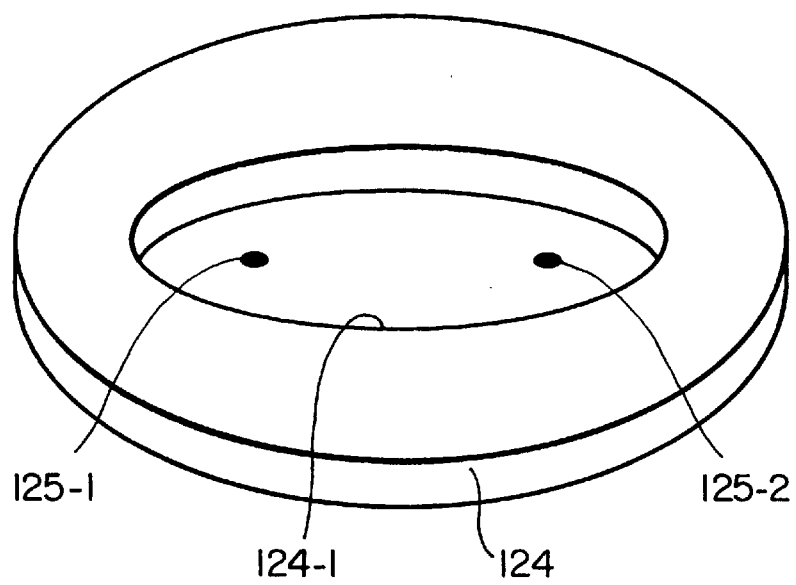
FIG_3C

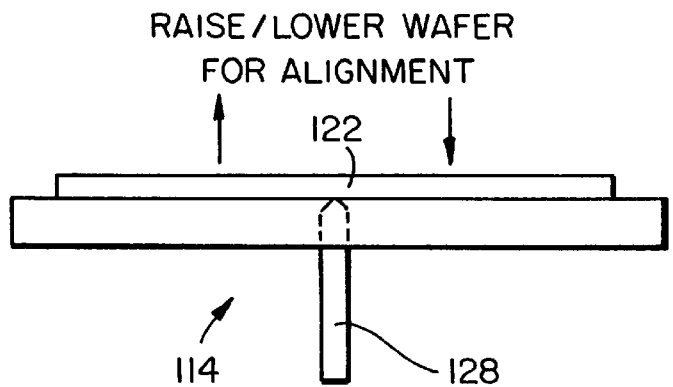
FIG_4
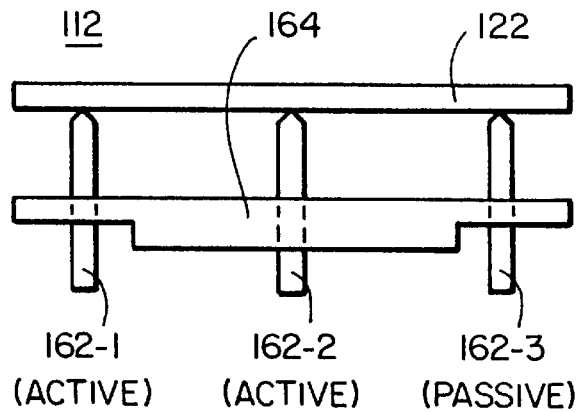
FIG_5A
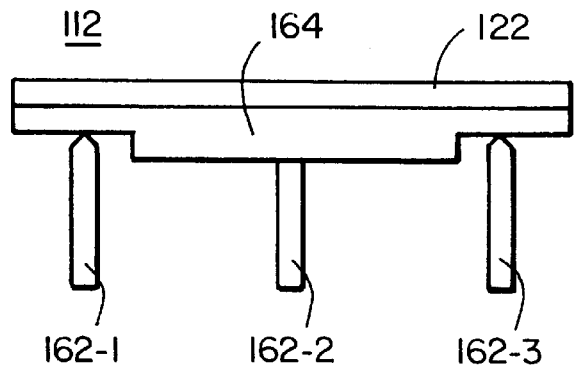
FIG_5B

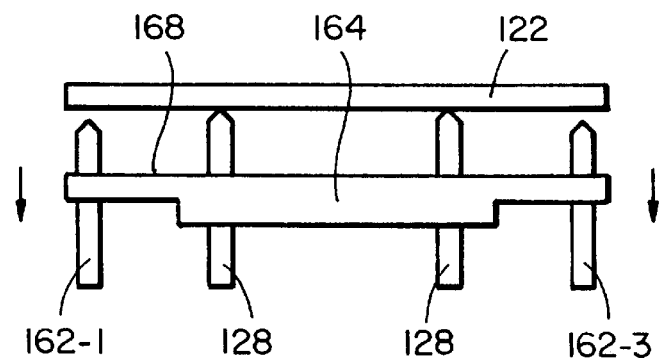
FIG_6A
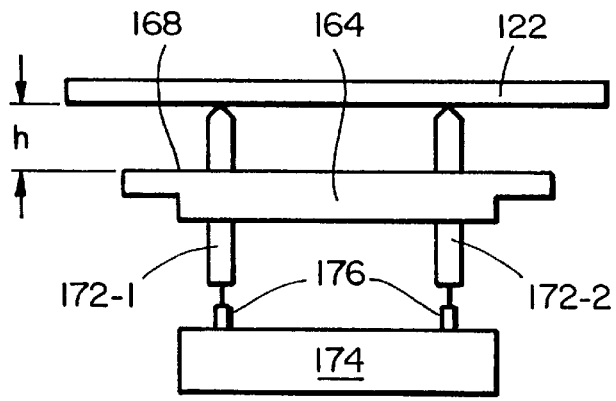
FIG_6B
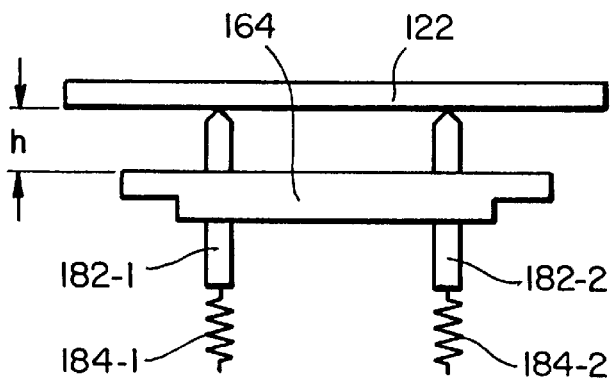
FIG_6C

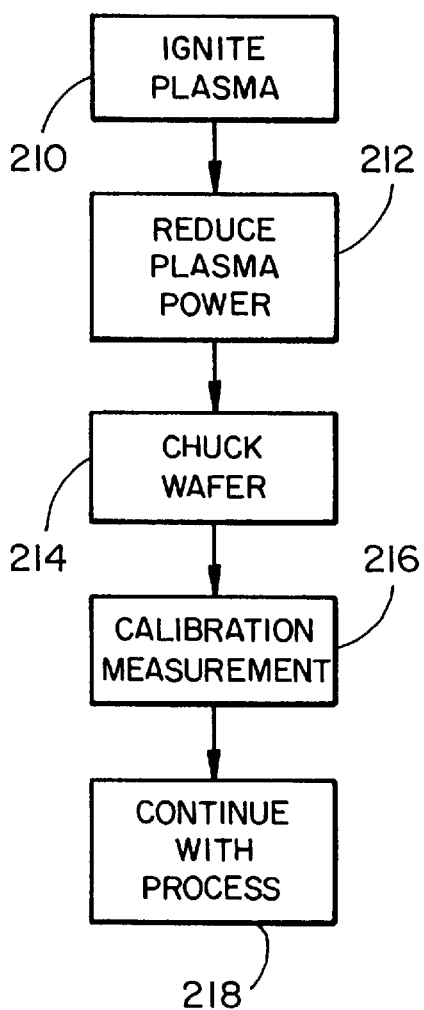
FIG_7
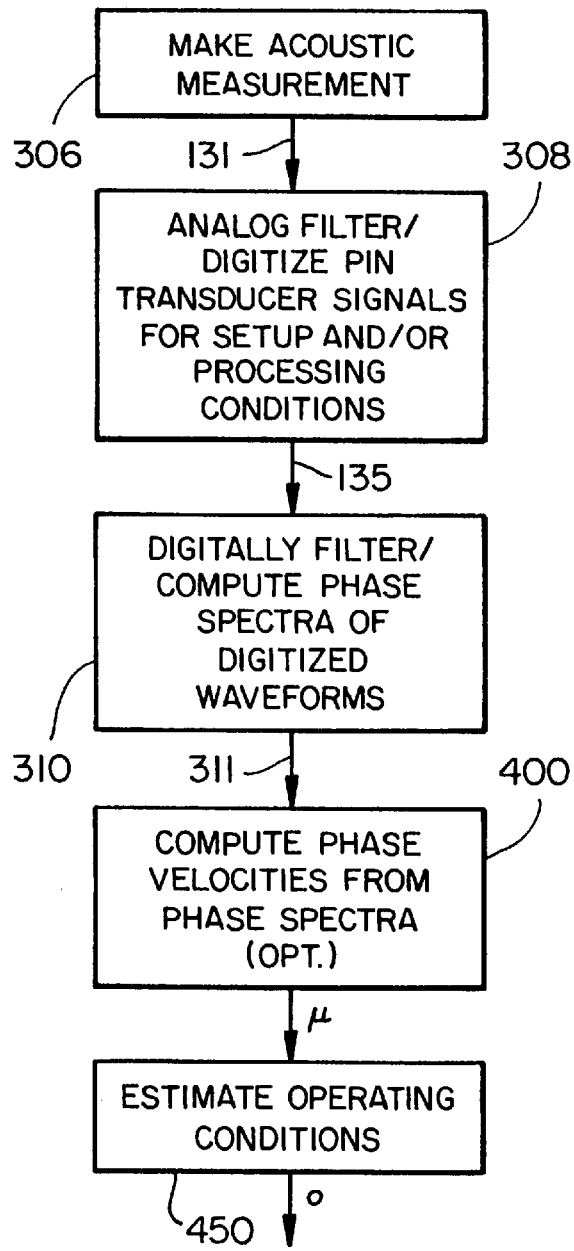
FIG_8

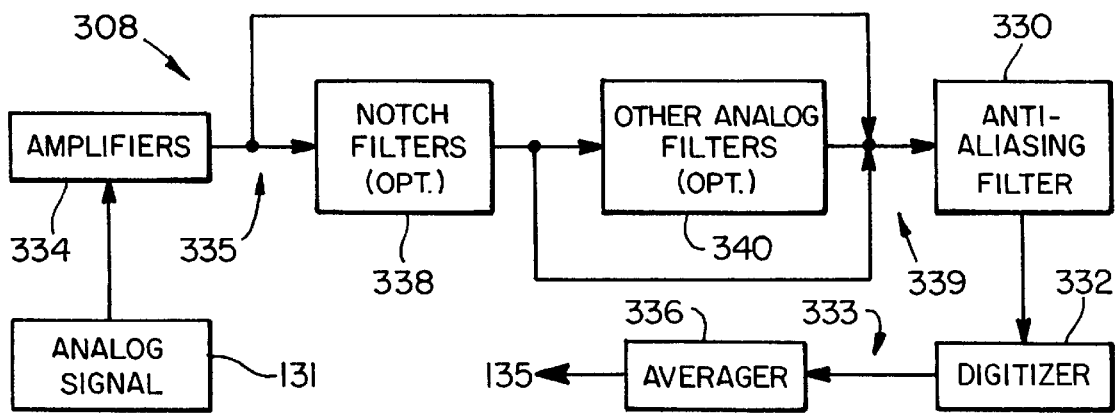
*FIG_9A*
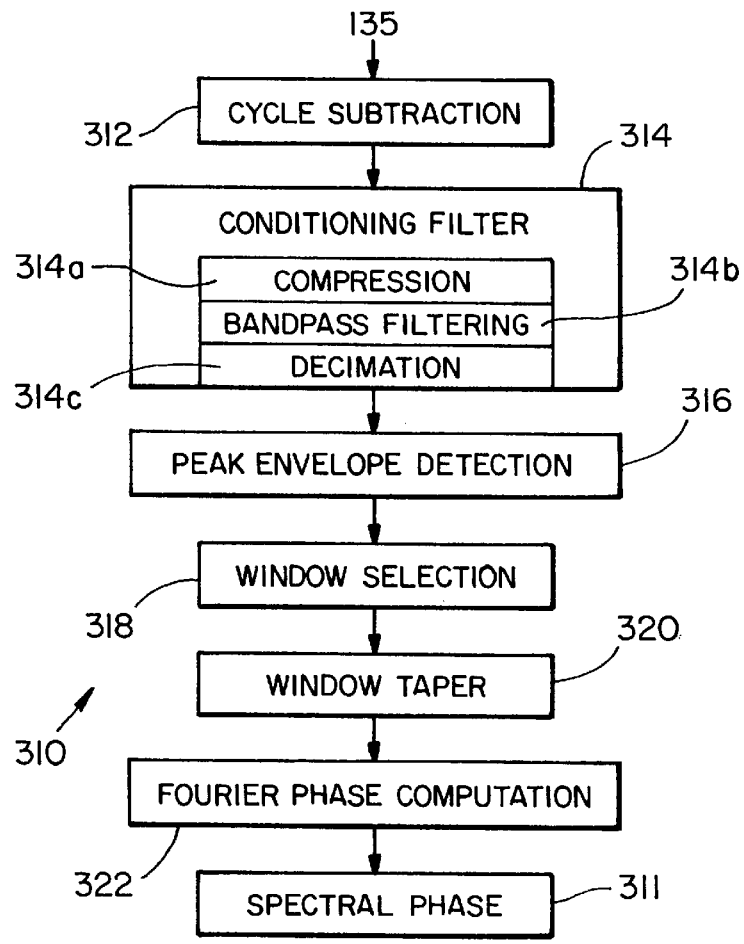
*FIG_9B*

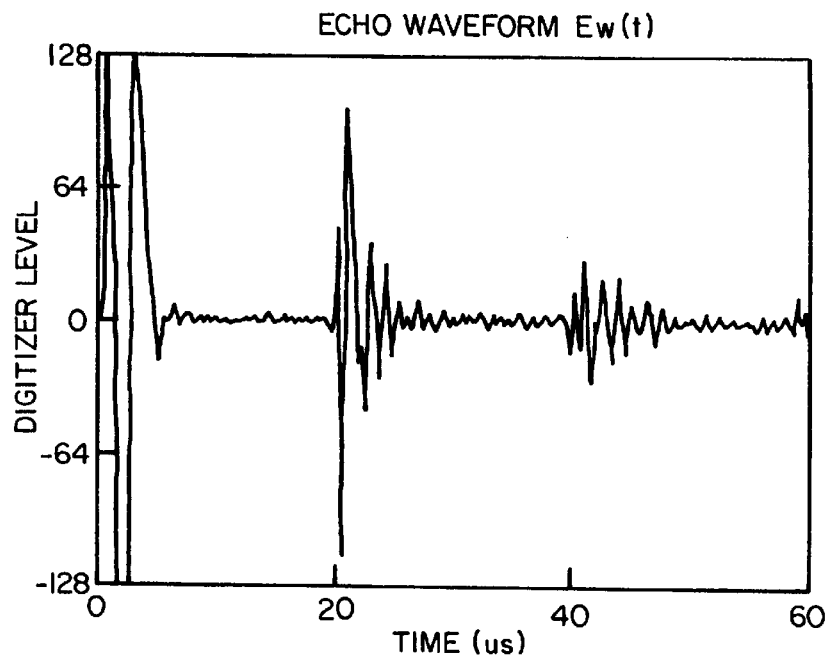
FIG_10A
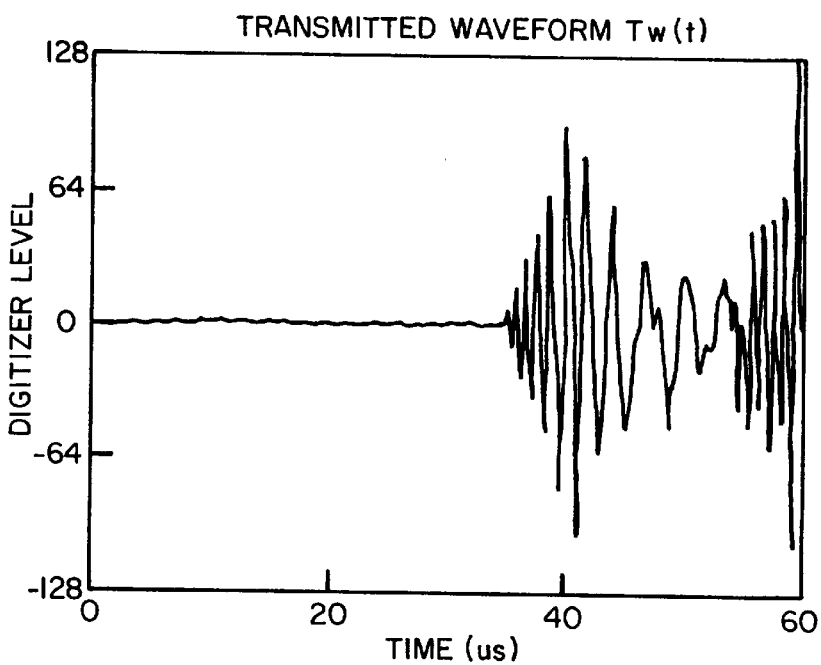
FIG_10B

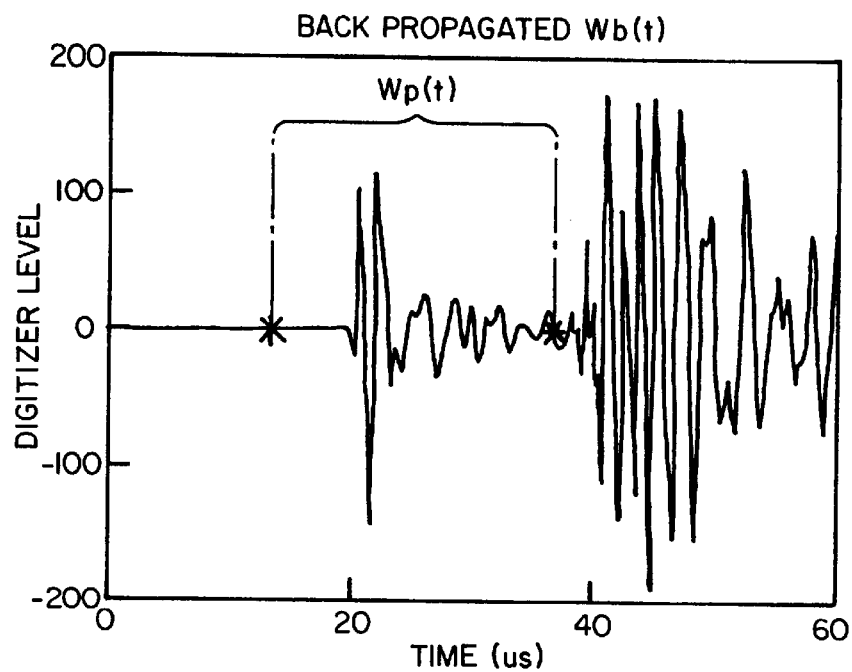
FIG_10C
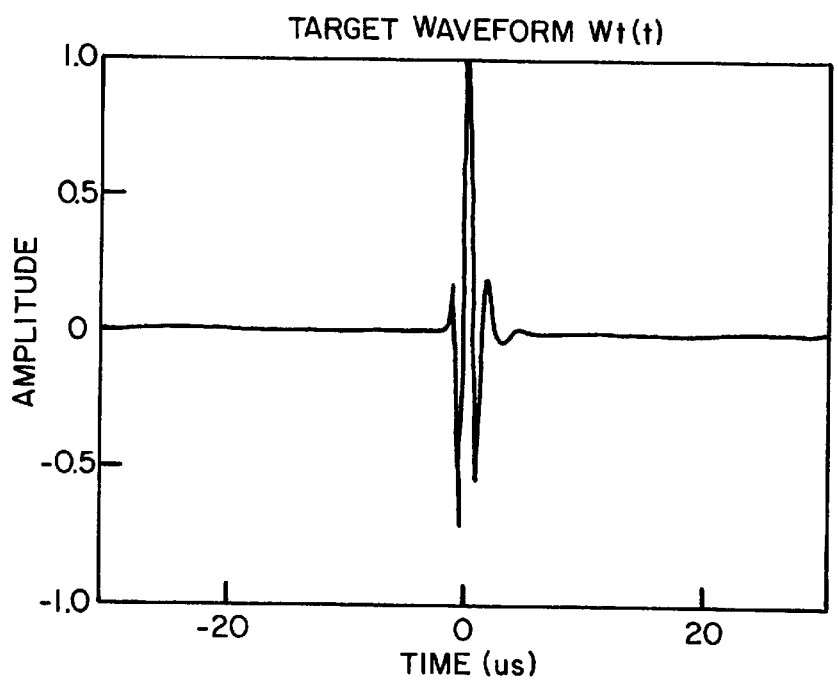
FIG_10D

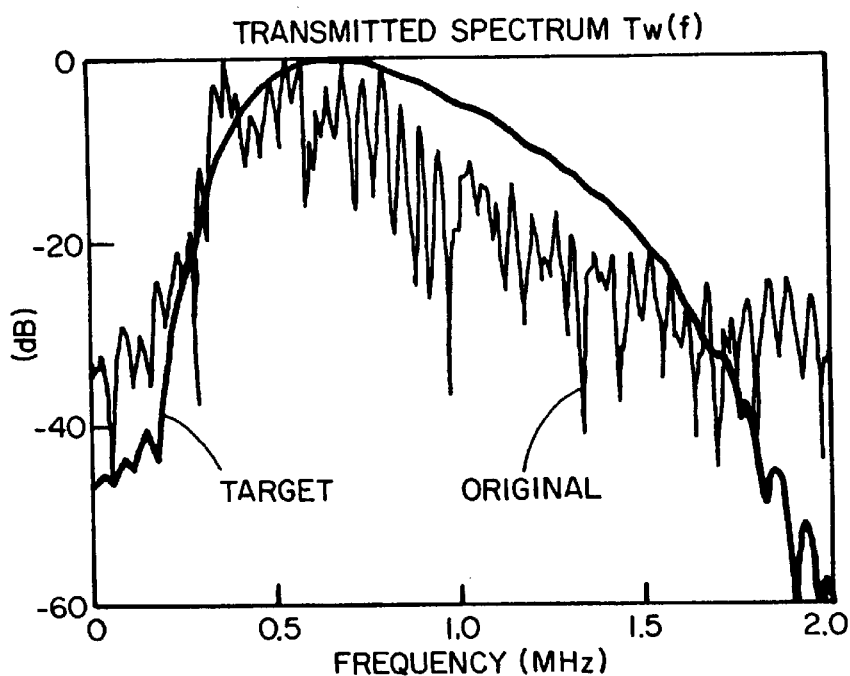
FIG_10E
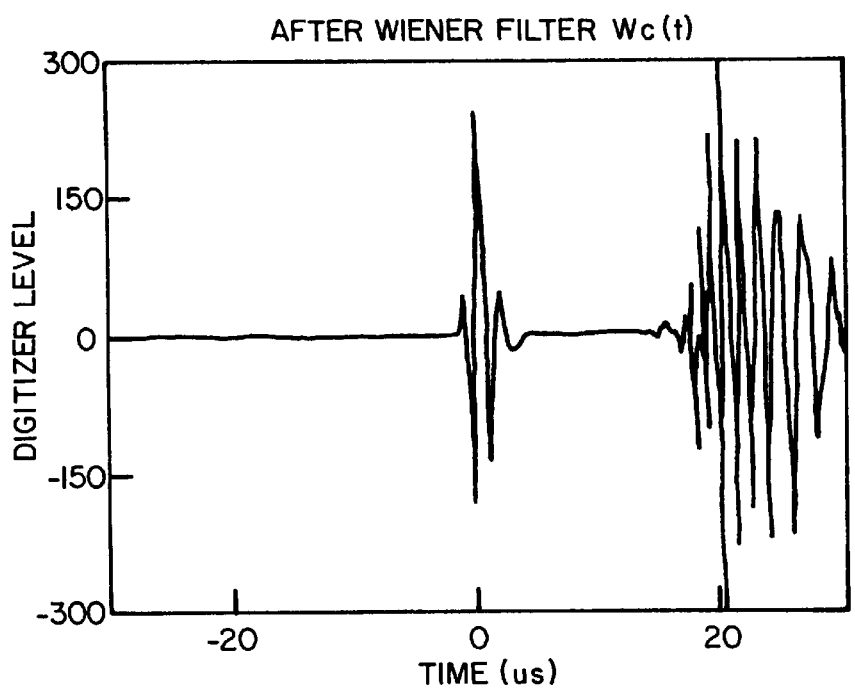
FIG_10F

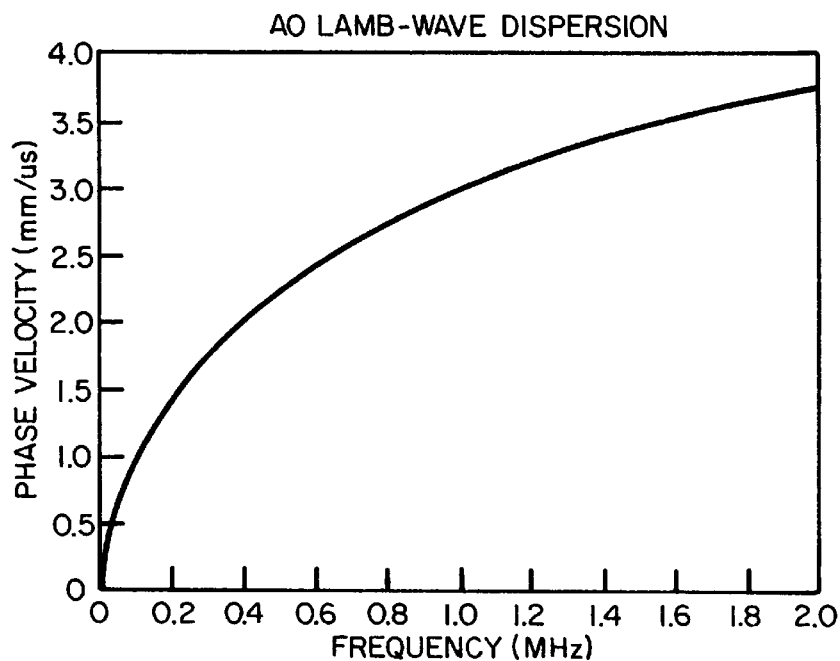
FIG_11
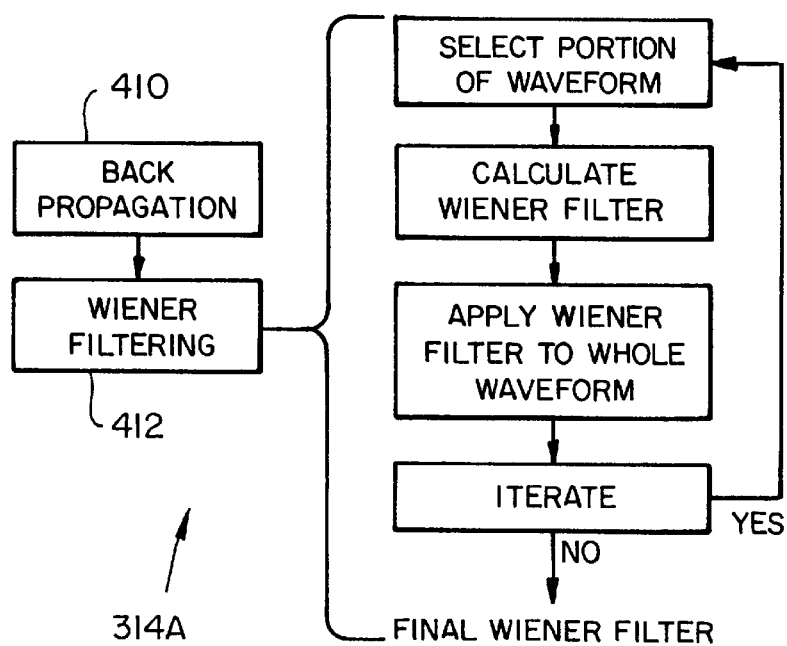
FIG_12

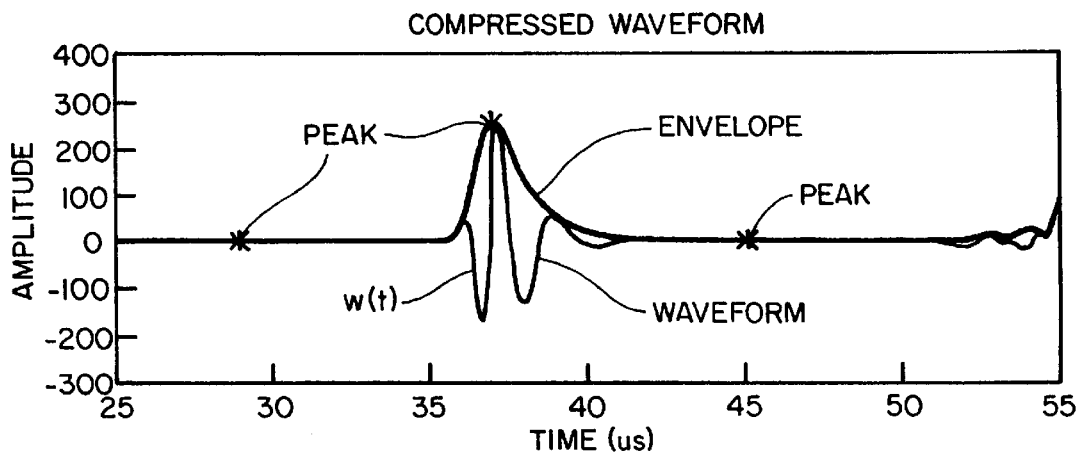
FIG_13A
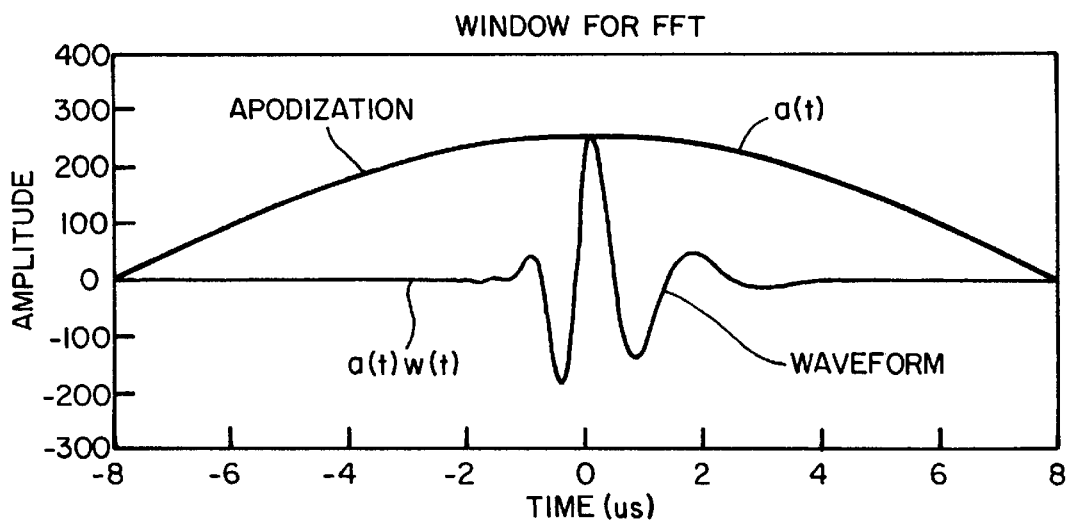
FIG_13B

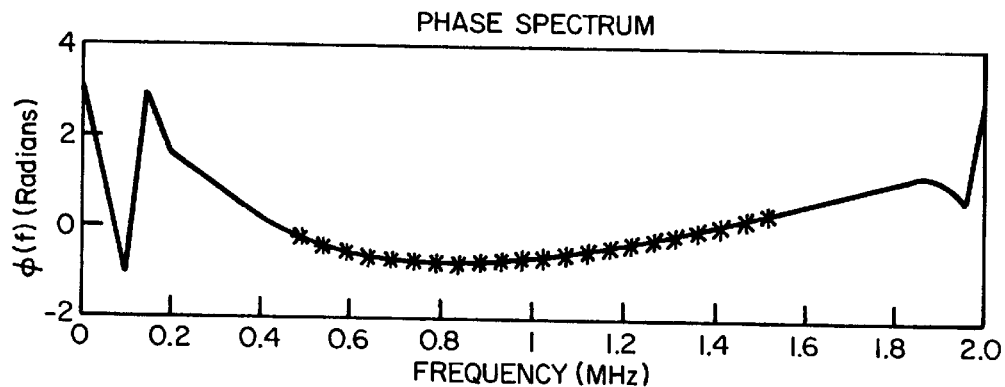
FIG_13C
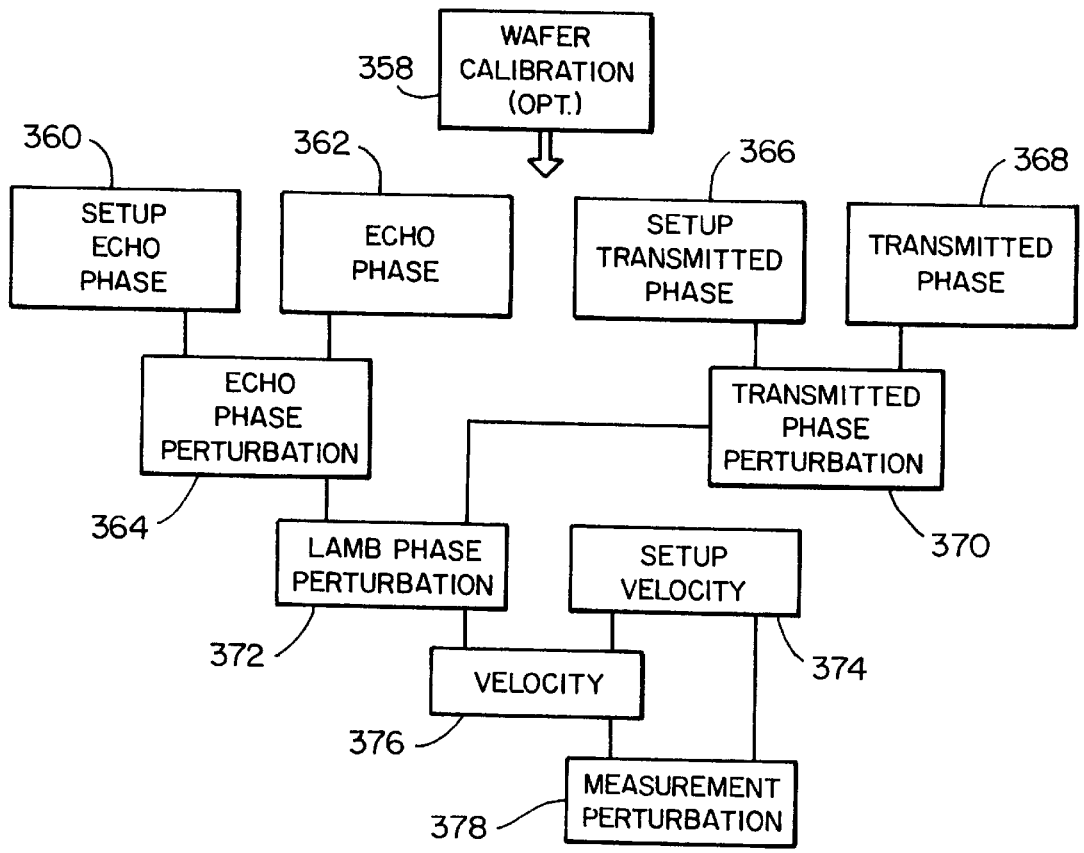
FIG_14

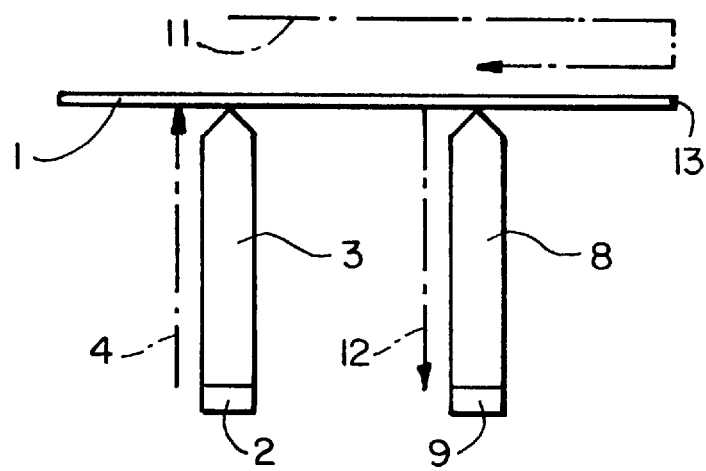
FIG_15
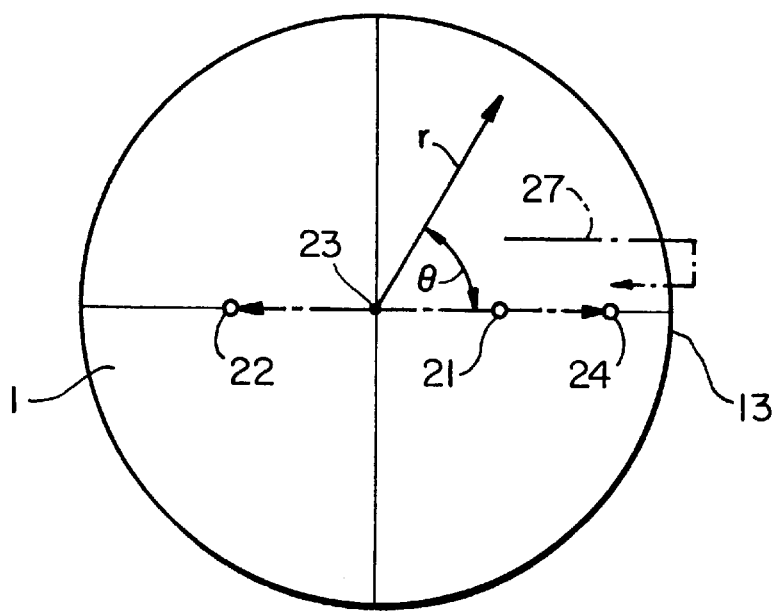
FIG_16

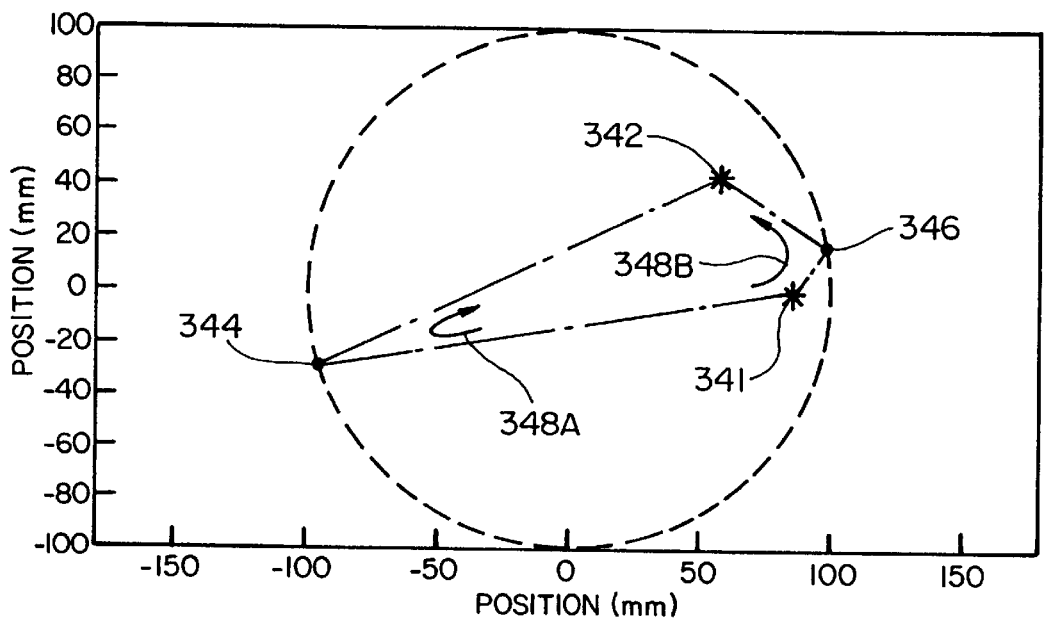
FIG_17A
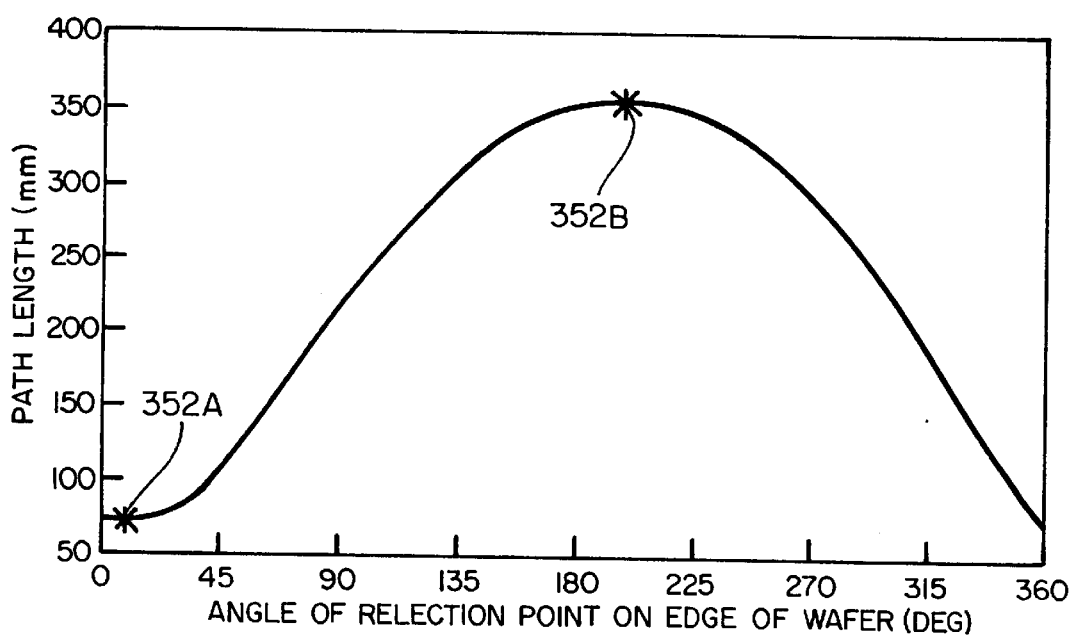
FIG_17B

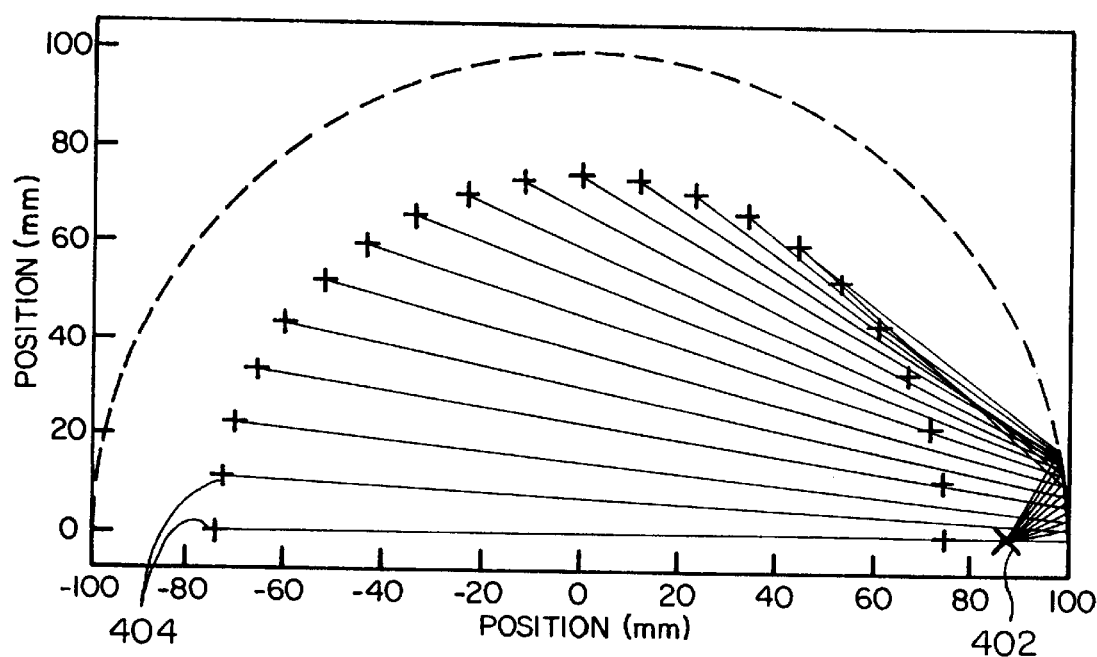
FIG_18A
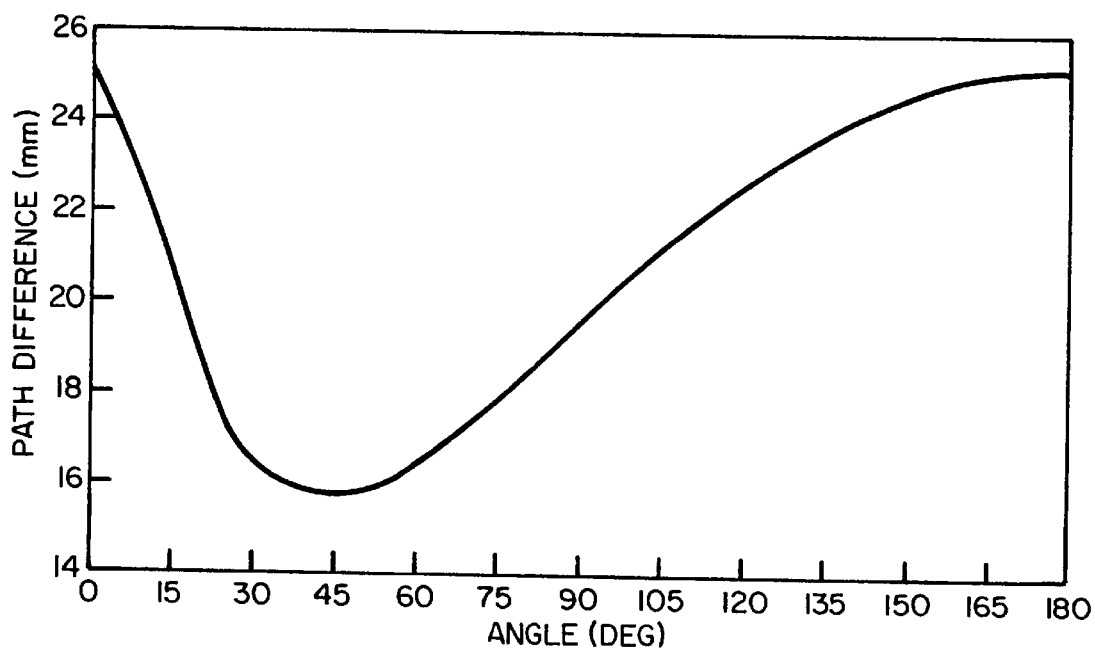
FIG_18B

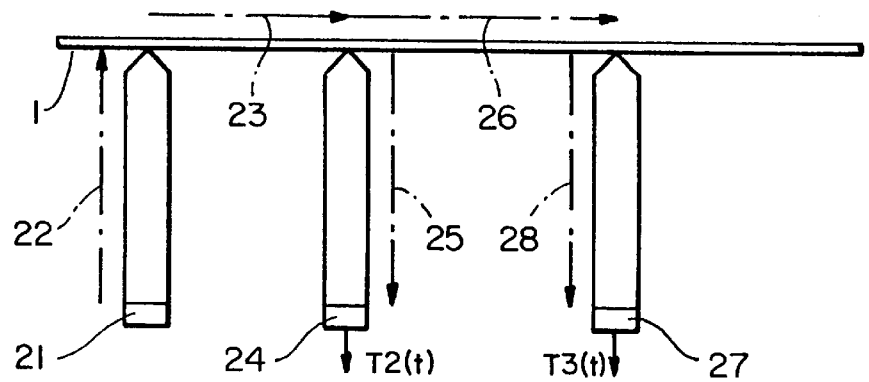
FIG_19
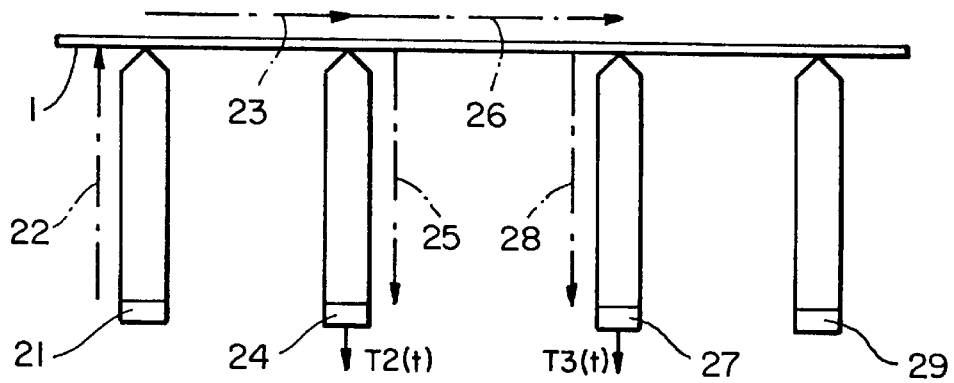
FIG_20A
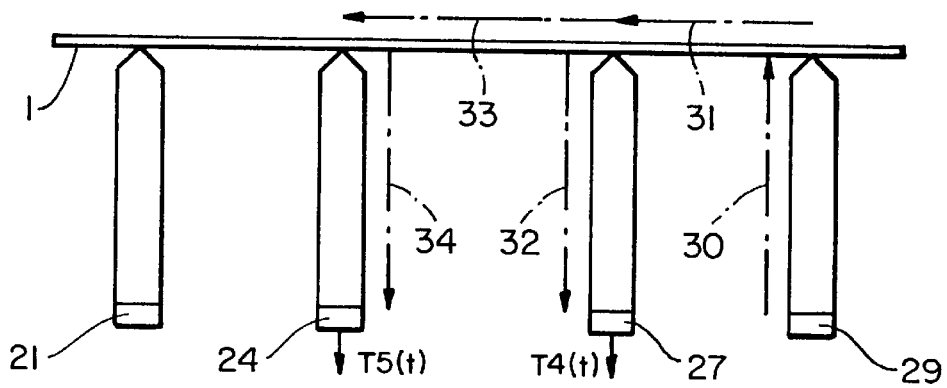
FIG_20B

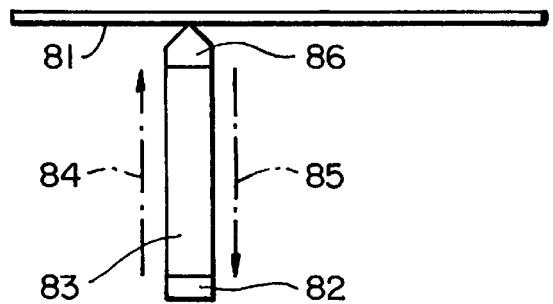
FIG_21
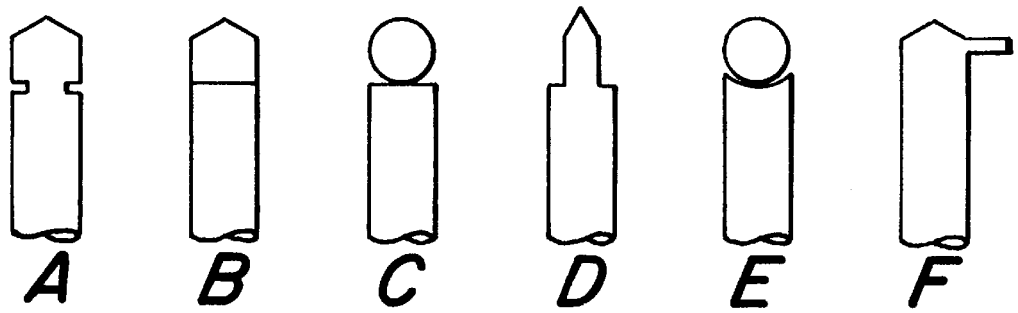
FIG_22
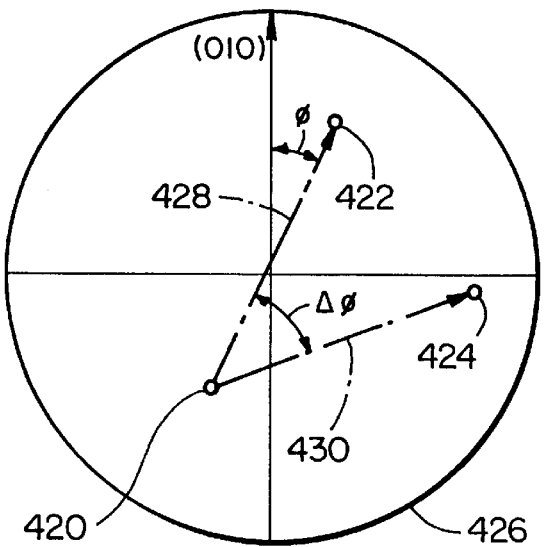
FIG_25

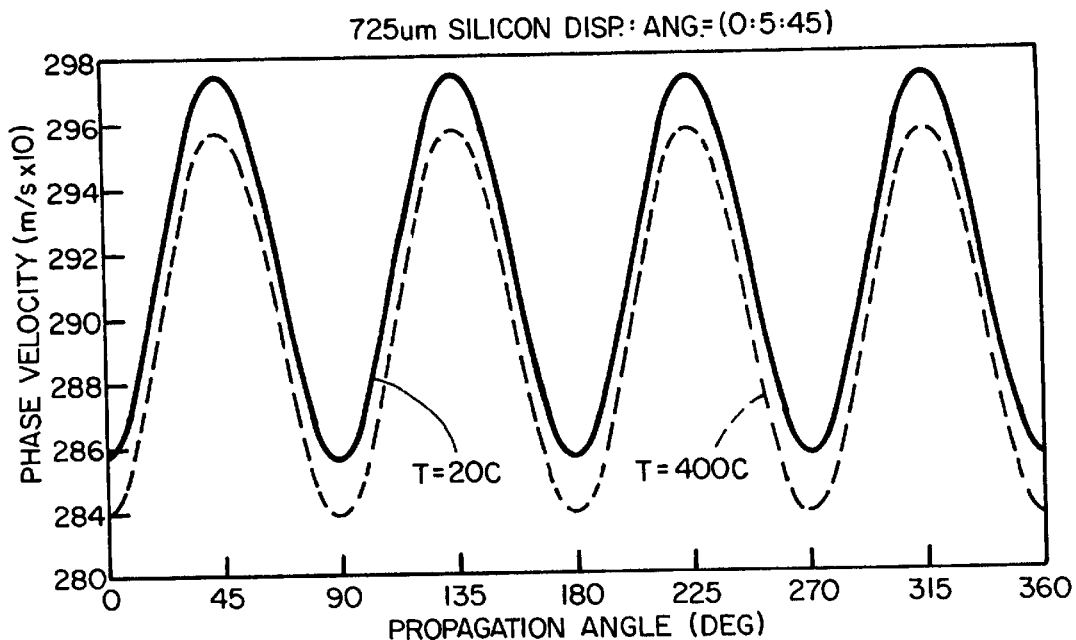
FIG_23A
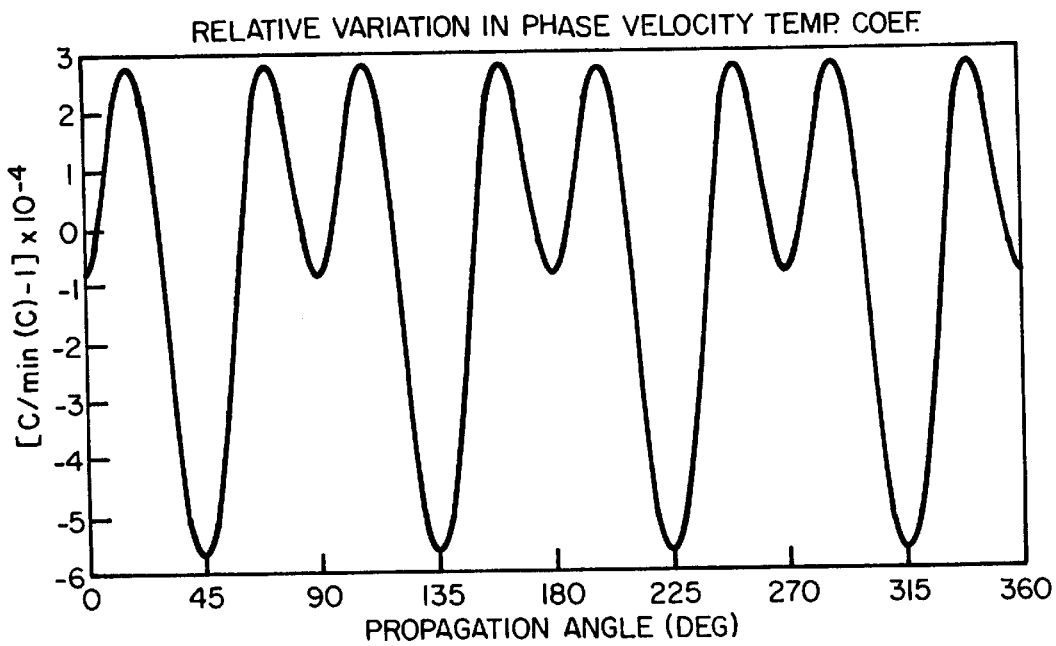
FIG_23B

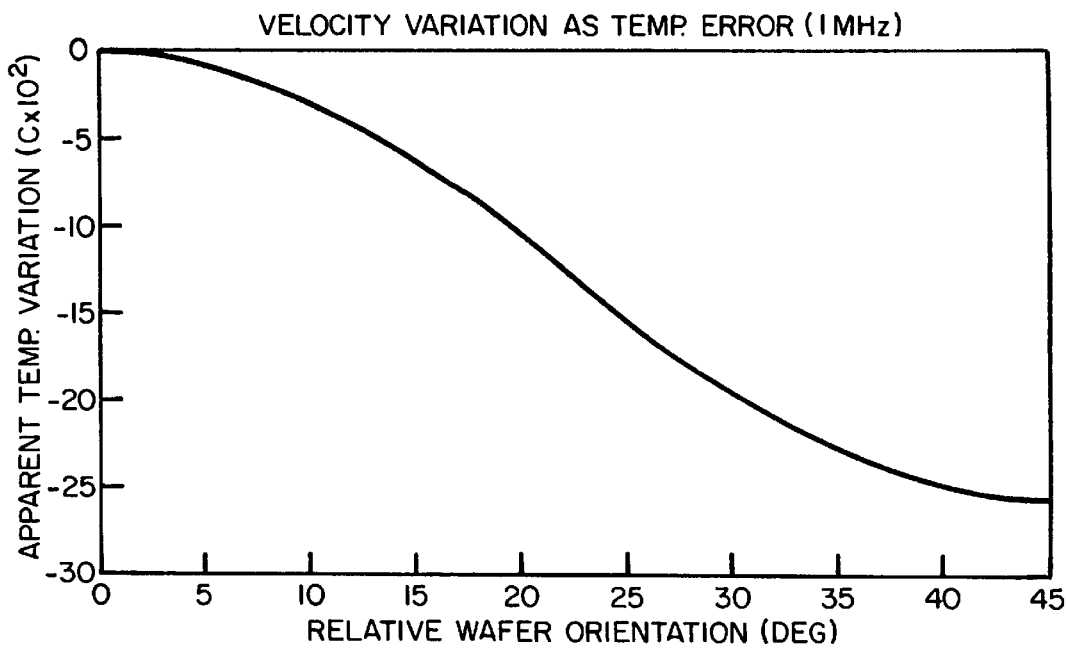
FIG_24
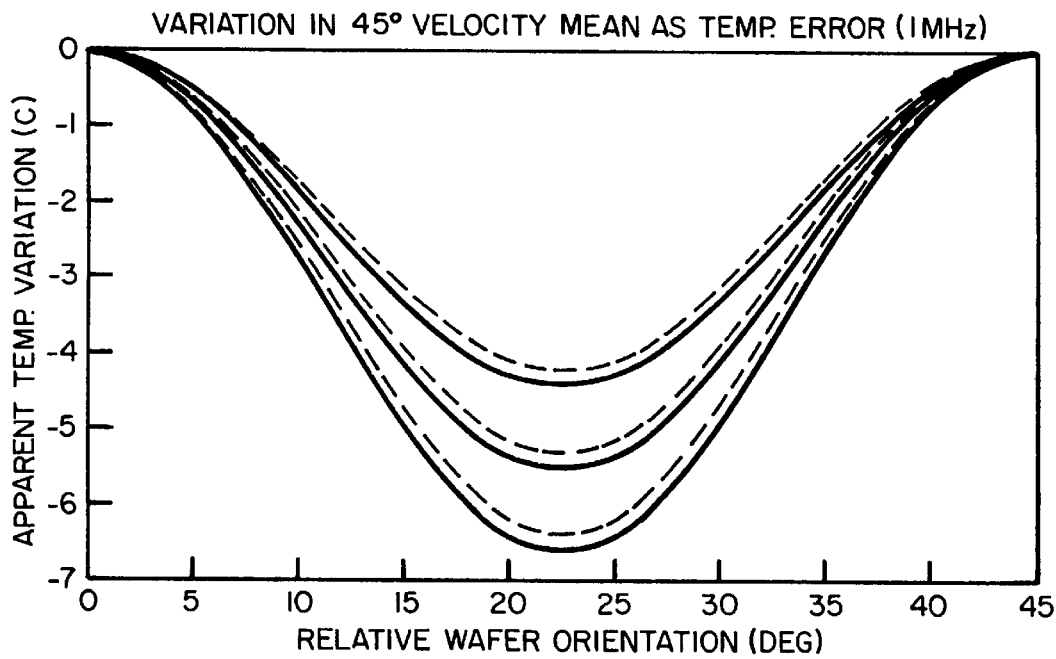
FIG_26

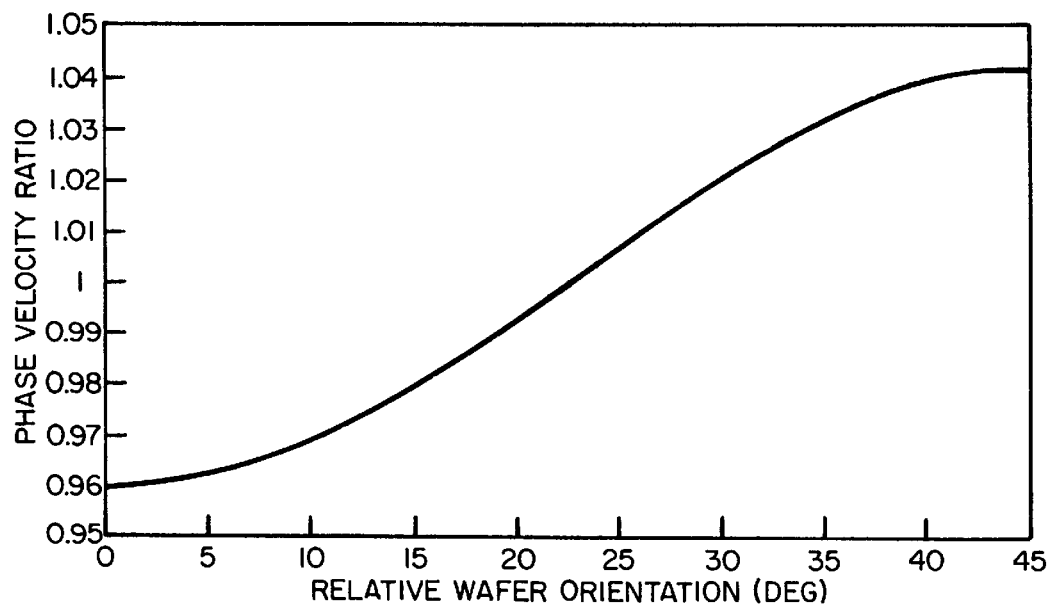
FIG_27
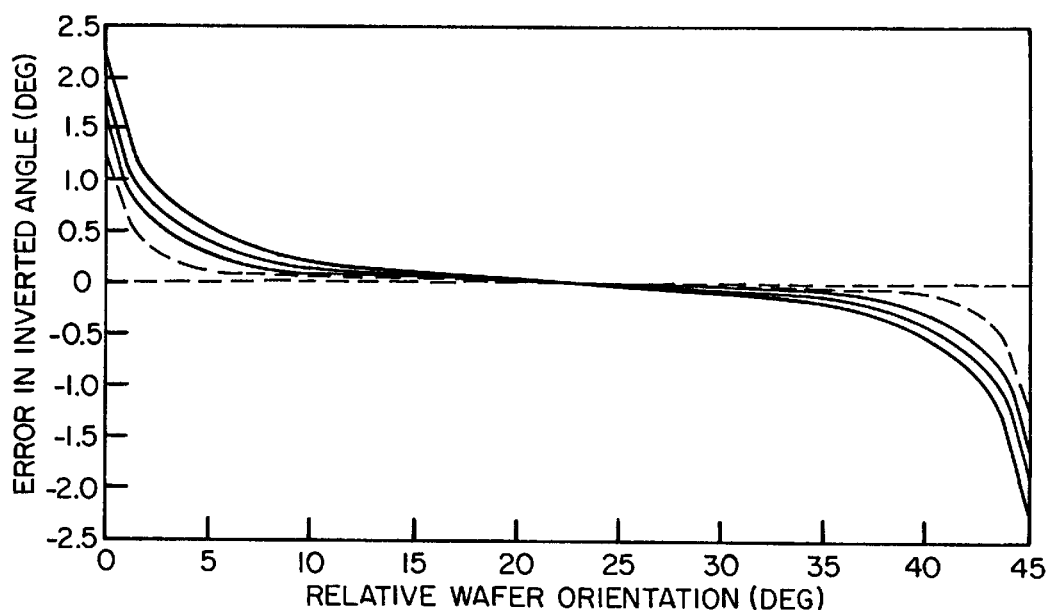
FIG_28

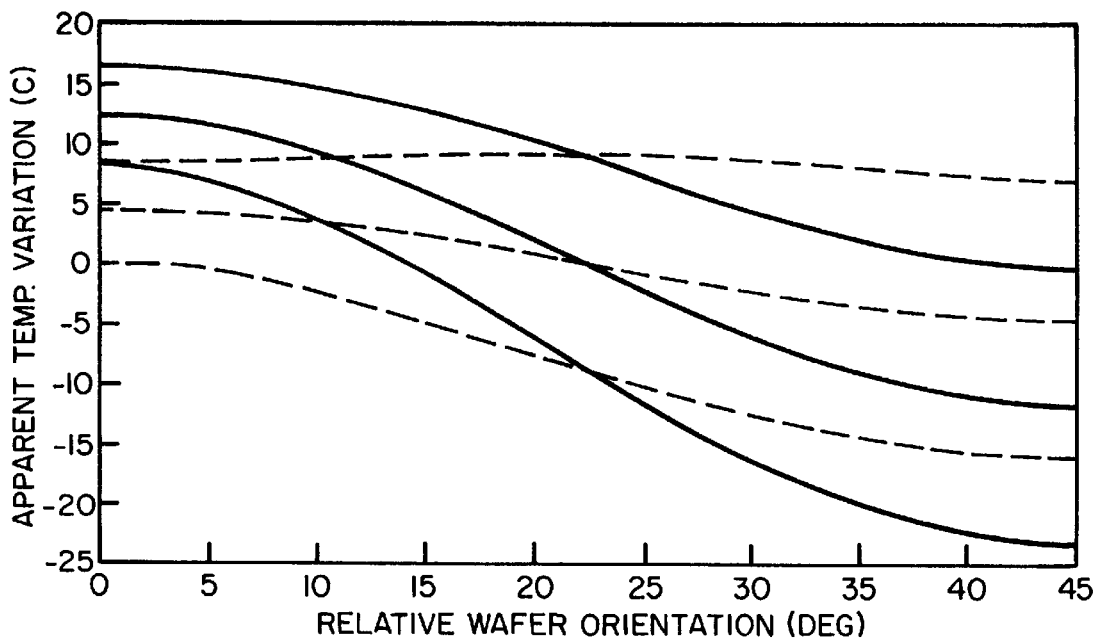
FIG_29
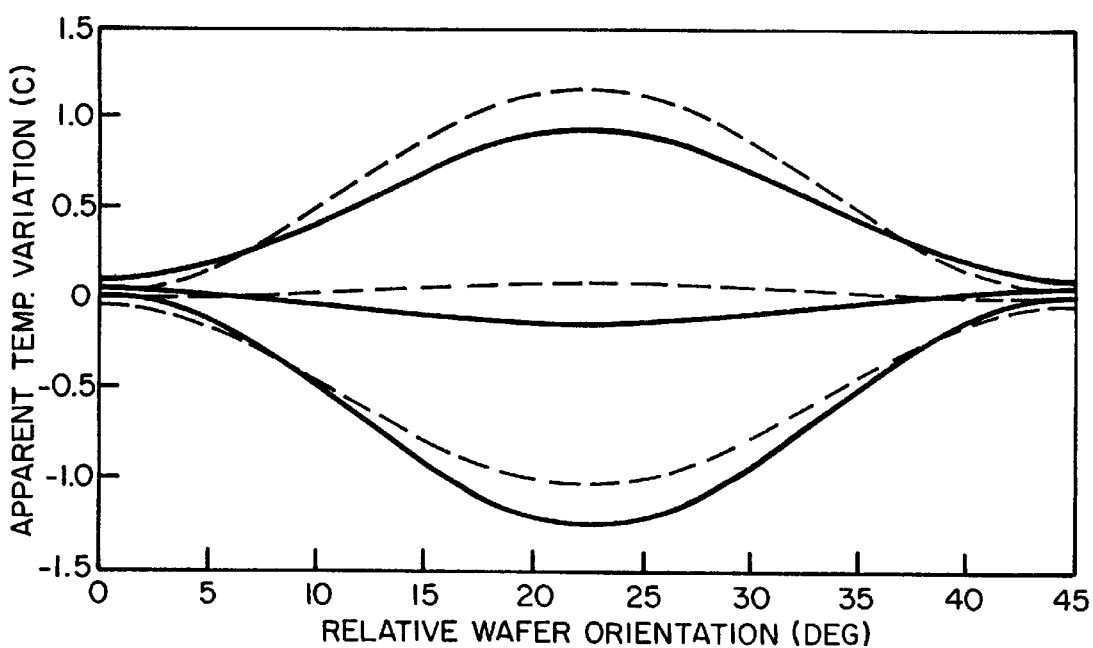
FIG_30

APPARATUS AND METHOD FOR CHARACTERIZING SEMICONDUCTOR WAFERS DURING PROCESSING

The present invention relates generally to ultrasonic transducers and particularly to pin transducers that use ultrasonic energy to determine a material's physical attributes, including temperature, thickness, density and the presence of defects.

BACKGROUND OF THE INVENTION

The present invention is an improvement of the system described in U.S. Pat. No. 5,469,742 ("Acoustic Temperature and Film Thickness Monitor and Method"). A goal of that prior art system was to monitor the temperature and/or thickness of a material during a semiconductor processing step without influencing the processing and with good survivability. The pin transducers described therein include an acoustic transducer at one end and a sharpened tip at the other end designed to contact a material to be monitored. In this system the transducer excites acoustic energy in the pin that is coupled by the tip into the material as Lamb or other acoustic waves. By monitoring the velocity of the Lamb waves in the material the thickness and/or temperature of the material can be determined (Lamb wave velocity varies with material thickness and temperature). The prior art system indirectly determines the Lamb wave velocity by measuring the time of flight of the Lamb waves between the (transmitting) pin that excited the Lamb waves and at least one receiving pin contacting the material.

This system measures the time between the occurrence of a predetermined zero crossing in the analog signal generated by an echo on the transmitting pin and the occurrence of pre-determined zero-crossing in the analog signal generated by the receiving transducer upon receiving acoustic energy excited in the receiving pin by a passing Lamb wave. The travel time of the acoustic energy in one of the pins is subtracted from the total time, yielding the time of flight between the transmitting pin and the particular receiving pin. Problems with this system include the need for sophisticated analog electronics to perform the necessary signal processing and errors due to differences between the pins.

Another problem with the prior art system described above and many other systems that use ultrasonic energy to monitor material characteristics is that they typically provide relative temperature and/or thickness measurements. I.e., these systems determine the change in a parameter and cannot absolutely determine a material parameter in practical situations.

SUMMARY OF THE INVENTION

In summary, the present invention is an apparatus and method for characterizing a semiconductor wafer during processing. In particular, the present invention includes a wafer characterization apparatus wherein one or more characteristics of a semiconductor wafer can be determined at one or more process times.

In the present invention, a set of measurements are made at an initial time when the one or more characteristics are known and a set of measurements are made at each of the process times, when at least one of the characteristics is not known. Perturbations in the one or more characteristics to be determined (i.e., changes from the known conditions at the initial time) are assumed to be related to the corresponding perturbations in the measurements via a known characterization sensitivity matrix.

In the preferred embodiment, each measurement is made by exciting acoustic waves in the wafer and then measuring indications of the waves' propagation in the wafer. The acoustic waves have propagation properties that vary depending on the wafer characteristics to be determined. Thus, the characterization sensitivity matrix describes the propagation properties of whichever type of acoustic waves are excited in the wafer.

In the preferred embodiment, the excited acoustic waves are Lamb waves, whose different frequency components have velocities that vary with characteristics of interest such as wafer temperature, thickness and structure or the states of films on the wafer. In this embodiment, the characterization sensitivity matrix describes how the different wafer and film characteristics change as a function of the frequency-dependent velocity. To ensure an accurate determination of one or more of the characteristics of interest at the process time a calibration procedure can be performed on each wafer being characterized when the conditions are known, to account for differences between wafers. To account for unknown aspects of the hardware used to make the measurements a setup procedure can also be performed wherein differences are determined in measurements made for known conditions. If the calibration and process measurements are performed with different hardware a hardware function is computed and then used to harmonize the measurements made during calibration and processing.

The present invention includes many different configurations for exciting and measuring the propagation of acoustic waves in a wafer or other test object. Most of the configurations employ at least one source transducer and at least one receiving transducer, where a source transducer excites acoustic waves in the wafer at an excitation point and the receiving transducer detects acoustic waves at a probe point. Specific configurations can include:

1. a SET configuration where there is exactly one source transducer and exactly one receiving transducer;
2. a DRP configuration where there is exactly one source transducer and at least two receiving transducers;
3. configurations where the source transducers and the receiving transducers are arranged so the excitation and probe points are on a diameter with respect to the surface of the wafer;
4. configurations where the receiving transducers and the source transducers are arranged so the probe points and the excitation points are collinear;
5. a SSRP configuration where there are two source transducers and two receiving transducers; and
6. configurations where at least one of the transducers is both a source and a receiving transducer.

Combinations of these configurations are possible. Also, in many of the configurations, in addition to measuring the propagation of the acoustic waves transmitted directly from a source to a receiving transducer, the propagation of acoustic waves reflected from a wafer edge can also be measured. In any of these cases, the paths over which propagation of the waves are measured corresponds to regions of the wafer for which the wafer characteristics are determined.

The transducers can be acoustic pin transducers that excite and detect waves through direct contact with the wafer. Each pin transducer includes a pin with a probe end that contacts the wafer and a piezoelectric element that converts acoustic waves in the pin to electrical signals and vice-versa. A source transducer can also be a laser beam directed at the excitation point. The receiving transducer can also be a laser detector configured to detect the passage of acoustic waves at the probe point.

The present invention incorporates an apparatus and method for correcting measurements that are made when the wafer's orientation is different from a preferred orientation. This is necessary to correct for velocity anisotropy in silicon wafers (i.e., the fact that the velocity of acoustic waves in silicon wafers varies with the angle between the measured propagation path and the preferred orientation. Corrections for anisotropy can be implemented in at least two ways. In a first preferred embodiment the characteristic is computed from an average of two measurements. In a second preferred embodiment, the orientation is estimated from two or more measurements and then the corrected characteristic is computed based on the estimated orientation of the wafer.

The present invention also teaches a system and method for measuring the temperature of a wafer using only a single transducer in contact with the wafer. In this system it is assumed that the temperature of the transducer is related to the temperature of the wafer. As a result, the temperature of the wafer can be determined by measuring the temperature of the transducer. A preferred transducer for this application includes a probe with a contact end configured to couple thermal energy between the wafer and the probe and a transducer end configured to convert acoustic energy in the probe to external electrical signals and vice-versa. In this embodiment an acoustic signal is excited in the probe by the transducer end and then the propagation properties of some portion of the probe are measured. The propagation properties are related to the temperature of the probe and therefore the temperature of the wafer. The probe can include a resonator that introduces an acoustic discontinuity near the contact end of the probe so as to restrict the temperature measurement in the probe to a location near the wafer. In this case, the frequency of the resonator during a measurement, which corresponds to the probe temperature, can be measured and used to estimate the wafer temperature.

The present invention includes a chuck that supports the wafer during processing steps and is configured so that, when characterization measurements are made while the wafer is chucked, the likelihood is reduced of the acoustic properties of the chuck influencing the acoustic waves propagating in the wafer and the resulting characterization measurements. In a preferred embodiment the side of the chuck contacting the wafer includes vias defined therein that are configured so that acoustic energy from the acoustic waves propagating in the wafer between the excitation and probe points is not coupled to the chuck.

BRIEF DESCRIPTION OF THE DRAWINGS

Additional objects and features of the invention will be more readily apparent from the following detailed description and appended claims when taken in conjunction with the drawings, in which:

FIG. 1 is a diagram of a prior art embodiment for performing acoustic characterization of semiconductor wafers using a sourcing and a receiving pin transducer (i.e., a SET configuration);

FIG. 2 is a view of a typical semiconductor wafer processing environment in which the present invention can be employed;

FIG. 3A is a block diagram of the present invention indicating measurement and processing structures;

FIG. 3B shows a preferred embodiment of the chuck 124 to illustrate structures for isolating the acoustic wafer measurements from acoustic characteristics of the chuck;

FIG. 3C shows a three-dimensional view of the chuck 124 of FIG. 3B;

FIG. 4 is a diagram of a preferred embodiment for performing calibration measurements while a wafer is being oriented in the orienter of FIG. 2;

FIG. 5A is a diagram of a preferred embodiment where calibration measurements are performed in a processing chamber using lift pins implemented as pin transducers in accordance with the present invention;

FIG. 5B is a diagram of the preferred embodiment of FIG. 5A where the calibration measurement has been completed and the wafer is secured to the chuck for processing;

FIG. 6A is a diagram of a preferred embodiment where calibration measurements and process measurements are made using pin transducers that project through the chuck and receive the wafer from the lift pins before the wafer is chucked;

FIG. 6B is a diagram of the preferred embodiment of FIG. 6A where pin transducer height above the wafer is controlled by an actuator;

FIG. 6C is a diagram of the preferred embodiment of FIG. 6A where pin transducer force against the wafer is controlled by a spring;

FIG. 7 is flow diagram indicating steps of a preferred embodiment where plasma power is reduced following ignition while calibration measurements are made;

FIG. 8 is a flow chart indicating steps employed in a preferred method for processing signals from pin transducers employed in an acoustic characterization system implemented in accordance with the present invention;

FIG. 9A is a flow chart showing additional details of the processing step 308 of FIG. 8 for transforming analog signals from one or more pin transducers into filtered, digital waveforms that can be processed by step 310 of FIG. 8;

FIG. 9B is a flow chart showing additional details of the processing step 310 of FIG. 8 for digitally filtering and computing the spectral phase of the digitized waveforms produced by step 308 of FIG. 8;

FIG. 10A is a plot of a typical, digitized, echo waveform received from a pin transducer such as the transducer 2 of FIG, 1;

FIG. 10B is a plot of a typical, digitized, transmitted waveform received from a pin transducer such as the transducer 9 of FIG, 1;

FIG. 10C is a plot of a digitized, transmitted waveform following a back-propagation operation performed by the conditioning filter 314 of FIG. 9B;

FIG. 10D is a plot of a target waveform that serves as a model of the transmitted waveform following signal processing;

FIG. 10E is a frequency-domain plot of the spectrum of the transmitted waveform before signal processing as compared to the spectrum of the target waveform from FIG. 10D;

FIG. 10F is a time-domain plot of the transmitted waveform following Wiener filtering which is performed by the conditioning filter 314;

FIG. 11 is a plot of the phase velocity of the lowest-order antisymmetric (A0 mode) Lamb wave;

FIG. 12 is a flow chart illustrating steps of the compression filter 314a of FIG. 9B;

FIG. 13A is a plot of the compressed waveform output by the conditioning filter 314 of FIG. 9B;

FIG. 13B is a plot of the FFT window and taper computed in the signal processing steps 318, 320 of FIG. 9B;

FIG. 13C is a frequency domain plot of the phase spectrum of the windowed waveform that is computed in the signal processing step 322 of FIG. 9B;

FIG. 14 is a flow diagram illustrating a preferred procedure used to estimate Lamb wave velocity given phase measurements of the transmitted and echo waveforms for setup and processing conditions;

FIG. 15 is a diagram of a preferred embodiment of the present invention that can be used to perform acoustic characterization of semiconductor wafers, including the use of an edge bounce measurement;

FIG. 16 is a diagram of a preferred embodiment of the present invention that can be used to perform acoustic characterization of semiconductor wafers, including the use of more than two pins;

FIG. 17A is a plot of edge bounce paths that come into play when reflection measurements are employed in the present invention;

FIG. 17B is a plot showing edge bounce path lengths as a function of the position of reflection points on the edge of the wafer;

FIG. 18A is a plot of edge bounce paths between the positions of a roving pin (marked with pluses "+") and another pin in a fixed position (marked with an "x");

FIG. 18B is a plot of edge bounce path difference as a function of edge bounce angle for the pin positions of FIG. 18A;

FIG. 19 is a diagram of a preferred differential receiver pair (DRP) acoustic characterization system geometry including a single sourcing pin and two receiving pins;

FIG. 20A is a diagram of a symmetric source and receiver pair (SSRP) acoustic characterization system geometry including two sourcing pins and two receiving pins where a first of the sourcing pins has been excited;

FIG. 20B is a diagram of the symmetric source and receiver pair (SSRP) acoustic characterization system geometry of FIG. 20A where the other of the sourcing pins has been excited;

FIG. 21 shows a preferred system for performing an acoustic characterization operation using a single pin transducer comprising an acoustic resonator;

FIGS. 22A–22F illustrate preferred resonator configurations for use in the system of FIG. 21;

FIG. 23A is a plot of Lamb wave phase velocity (m/s) versus Lamb wave propagation angle (degrees) with respect to a preferred wafer orientation for a 725 $\mu$m thick silicon wafer measured at temperatures of 20 C and 400 C;

FIG. 23B is a plot of the relative variation in the Lamb wave phase velocity/temperature coefficient (C/min(C)−1) for the system of FIG. 23A;

FIG. 24 is a plot of apparent temperature error caused by anisotropy at 1 MHz for wafer thickness/temperature combinations of (706.875 $\mu$m, 20 C), (725 $\mu$m, 20 C), (743.125 $\mu$m, 20 C), (706.875 $\mu$m, 20 C), (725 $\mu$m, 20 C) and (743.125 $\mu$m, 20 C); the error is symmetrical about 45 degrees and repeats every 90 degrees;

FIG. 25 depicts a configuration of three pins that can be employed to correct for anisotropy when the wafer orientation $\phi$ is not known a priori;

FIG. 26 is a plot of the apparent temperature variation (i.e., error) resulting from variation in the 45 degree velocity mean for Lamb waves at $_1$ MHz and for wafer thickness/temperature combinations of (706.875 $\mu$m, 20 C), (725 $\mu$m, 20 C), (743.125 $\mu$m, 20 C), (706.875 $\mu$m, 400 C), (725 $\mu$m, 400 C) and (743.125 $\mu$m, 400 C); the error is symmetrical about 45 degrees and repeats every 90 degrees;

FIG. 27 is a plot of the ratio of phase velocity and temperature measured at 45 degrees versus relative wafer orientation $\phi$ for Lamb waves at 1 MHz and for wafer thickness/temperature combinations of (706.875 $\mu$m, 20 C), (725 $\mu$m, 20 C), (743.125 $\mu$m, 20 C), (706.875 $\mu$m, 400 C), (725 $\mu$m, 400 C) and (743.125 $\mu$m, 400 C); the error is symmetrical about 45 degrees and repeats every 90 degrees;

FIG. 28 is a plot of the error in the estimated wafer orientation derived by inverting the phase-velocity ratios from FIG. 27 for Lamb waves at 1 MHz and for wafer thickness/temperature combinations of (706.875 $\mu$m, 20 C), (725 $\mu$m, 20 C), (743.125 $\mu$m, 20 C), (706.875 $\mu$m, 400 C), (725 $\mu$m, 400 C) and (743.125 $\mu$m, 400 C); the error is symmetrical about 45 degrees and repeats every 90 degrees;

FIG. 29 is a plot of the apparent temperature variation (i.e., error) in a temperature after correction based on the estimated wafer orientation for Lamb waves at 1 MHz and for wafer thickness/temperature combinations of (706.875 $\mu$m, 20 C), (725 $\mu$m, 20 C), (743.125 $\mu$m, 20 C), (706.875 $\mu$m, 400 C), (725 $\mu$m, 400 C) and (743.125 $\mu$m, 400 C); the error is symmetrical about 45 degrees and repeats every 90 degrees; and FIG. 30 is a plot of the apparent temperature variation (i.e., error) in an error-corrected 45 degree velocity mean for Lamb waves at 1 MHz and for wafer thickness/temperature combinations of (706.875 $\mu$m, 20 C), (725 $\mu$m, 20 C), (743.125 $\mu$m, 20 C), (706.875 $\mu$m, 400 C), (725 $\mu$m, 400 C) and (743.125 $\mu$m, 400 C); the error is symmetrical about 45 degrees and repeats every 90 degrees.

DESCRIPTION OF THE PREFERRED EMBODIMENTS

Before the preferred embodiments are described, the following glossary is provided to define some of the terms associated with the present invention.

Glossary calibration
    a characterization step that is performed on a wafer at a calibration station when all relevant operating conditions are known. The idea of the calibration measurement is to account for wafer-to-wafer differences by determining for each individual wafer being processed the measurements that result from characterizing that wafer for the known operating conditions and to determine therefrom individual Lamb wave propagation characteristics in that wafer. These characteristics are used to estimate an unknown process condition from characterization measurements made during a processing step in a processing chamber.

characterization sensitivity
    the inverse operator of the effect of operating conditions on a measurement;

echo
    an acoustic wave reflected away from a boundary (e.g., the end of a pin) in response to an incident acoustic wave interacting with the wafer.

Lamb wave
    an acoustic wave in thin substrates. Lamb wave modes are dispersive. Preferred Lamb wave modes for use in the present invention include the lowest-order antisymmetric (or A0) and symmetric (or S0) waves.

measurement
    a vector quantity operated on by a characterization sensitivity to yield an estimate of a wafer's operation condition perturbation.

pin transducer
    an electro-acoustic measurement system consisting of an acoustically-transmissive pin and an electro-acoustic transducer. When used as a source, sound waves set up in the pin by the transducer are transferred by the pin into a target. When used as a receiver, sound waves in the target excite waves in the pin which are coupled to the transducer.
receiver
    a generic term for a system that can sense acoustic waves in a target. The receiver might be a pin transducer, a laser-based sensing device or any other appropriate technology.
setup
    a means of removing the characteristics of the transducers (sources and receivers) from the measurements intended to characterize the wafer. Typically a setup measurement is made for known wafer characteristics and subtracted from measurements made for wafers with unknown characteristics.
source
    a generic term for a system that can excite acoustic waves in a target. The source might be a pin transducer, a laser-based excitation device or any other appropriate technology.
transmission profile
    an intermediate result derived from a waveform prior to calculating a measurement that is inverted by a characterization sensitivity. It generally characterizes the propagation of the transmitted waveform.

Referring to FIG. 1, there is shown a schematic diagram of a basic, acoustic characterization system geometry employed by the present invention, wherein the temperature, or other characteristic, of a wafer 1 is determined using a sourcing (i.e., transmitting) pin transducer comprising a sourcing pin 3 and transducer 2 and a receiving pin transducer comprising a receiving pin 8 and transducer 9. In addition to semiconductor wafers 1, the teachings of the present invention are equally applicable to other types of substrates/test objects. As a result, all references hereinafter to "wafers" shall be understood to apply to any test objects in which the acoustic measurements described herein can be performed. Possible test objects include plates, metallic skins, pipes, and micromachined structures. Similarly, the discussion herein of "Lamb waves" shall be understood to mean waves that are supported by a test object; e.g., Rayleigh waves on thick objects and torsional waves, etc. on rods.

In an exemplary implementation, a short-duration (i.e., on the order of microseconds) voltage applied to the sourcing piezoelectric element 2 causes it to vibrate. The vibration in element 2 in turn excites an acoustic wave 4 (in the preferred embodiment, an extensional wave) that propagates up the sourcing pin 3. When the wave 4 reaches the top of pin 3, after a period of on the order of tens of microseconds, it excites two waves: an echo 5, which propagates back down pin 3, and a cylindrically expanding Lamb wave on the wafer 1 that reaches a receiving pin 8 via a wave path 6. The echo 5 reaches the bottom of the sourcing pin 3 and excites an echo waveform EW(t) across the element 2. A waveform (e.g., the echo waveform EW(t)) is a time-varying voltage at the terminals of a piezoelectric element (e.g., the element 2). When the Lamb wave reaches the receiving pin 8, it excites a wave 7 that propagates down pin 8 to reach a receiving piezoelectric element 9. The element 9 produces, in response, a transmitted waveform TW(t). There are many variations of this basic measurement, some of which are described below.

The velocity of each Lamb wave is sensitive to the temperature of the medium in which it is propagating. Consequently, the path 6 (of the transmitted waveform TW(t)) has the desired sensitivity for measuring temperature in the wafer and the paths 4 and 7 (of TW(t)) have undesired sensitivities (in this measurement) to the temperature of the pins 3 and 8. The undesirable sensitivity to pin temperature can be substantially reduced by simultaneously processing a group of waveforms consisting of at least the transmitted waveform TW(t) and one echo waveform EW(t). The group of waveforms can include additional waveforms as well, such as waveforms from other transducers (e.g., operating at different temperatures), and/or waveforms arising from different modes of propagation on the wafer, and/or echo waveforms from every pin contributing to the group of waveforms. With this method all of the waveforms in the group are collected at substantially the same time on a time scale appropriate to the heating of the wafer, (e.g., on the order of 0.1 to 1 seconds).

In this and other geometries a goal of the present invention is to measure the wafer temperature absolutely by measuring changes in waveforms that have propagated over some acoustic path S (e.g., the path 6 for the geometry in FIG. 1). To a reasonable level of accuracy, a measured temperature $\bar{T}$ is approximately equal to an average of temperatures T(r) over the acoustic path S; i.e., $$\bar{T} = \frac{1}{|S|} \int_S T(r) ds,$$

where $|S|$ is the length of S and r is the vector specifying position on the wafer. While this ray approximation is not strictly true (i.e., the region of integration should have some width as well as length), it is a useful simplification that describes the operation of the various preferred embodiments.

A. Measurement and Inversion Strategy
Perturbation Approach

The goal of the present invention is to estimate the operating condition, expressed as the vector O of the wafer from a vector of measurements M based on processing the waveform group. The strategy is to estimate perturbations of the operating condition from some setup condition $M_0$ (in which a group of setup waveforms were recorded) via perturbations in the measurements. Processing of each waveform group yields a vector of $N_M$ measurements M={$M_i$}, i=1,2, ..., $N_M$. The measurements might be functions of the phases of various Fourier spectral components of waveforms in the group, or functions of one or more times of arrival, e.g., the times of selected zero crossings. The processing of a setup waveform gives the setup measurement M0I The operating condition O={$O_j$}, j=1,2, ..., $N_O$ includes implicitly only those conditions that are of interest. Candidates for specific operating conditions as members of the vector include:

(1) the wafer's temperature,
(2) the pins' separation,
(3) the wafer's thickness, and
(4) the properties of layers on the wafer (e.g., thickness or state of polymerization).

It is possible for O to have a single member, e.g., the wafer's temperature or thickness. All candidate conditions that are not included in O are assumed to be known and invariant, or irrelevant. The setup operating condition $O_0$ must be known, a priori, and other operating conditions are to be estimated. The measurement perturbation $\mu=M-M_0$ is related to the operating perturbation $o=O-O_0$ by a function $\Lambda$, such that $\mu=\Lambda(o)$, which is determined by the physics of Lamb wave propagation. The acoustic characterization of the wafer is performed by inverting the function $\Lambda$ to obtain a characterization sensitivity $\Lambda^{-1}$ which, along with the measurement perturbation and setup operating condition yields the operating condition matrix $O=\Lambda^{-1}(\mu)+O_0$. Any intermediate results of processing waveforms to yield measurements are termed transmission profiles.

In the preferred embodiments described herein a linearized, matrix version L of $\Lambda$ is used that establishes a linear relationship between the measurement perturbation and the operating perturbation; i.e., $\mu \cong Lo$. After inverting L to obtain a linear characterization sensitivity matrix $L^{-1}$, the operating condition O can be estimated as $O \cong L^{-1}\mu+O_0$. In order to estimate the operating perturbation o, $L^{-1}$ must be estimated from a set of either real or numerical experiments, possibly by first estimating L and then inverting it. Many strategies are possible for determining $L^{-1} \approx \Lambda^{-1}$.

A preferred strategy for estimating the characterization sensitivity $L^{-1}$ is to perform a set of $N_O$ numerical experiments. In each experiment all of the operating conditions but one are kept the same as the setup conditions. The operating condition for a kth experiment can be represented as the kth column, $o_k$, of the following matrix, where $O_{jk}$ is the perturbation to the kth operating condition:

$$o_{jk} = \begin{cases} \text{zero for } j \neq k \\ \omega_k \text{ for } j=k \end{cases}$$

Each column $\{L_{ik}, i=1 \ldots N_M\}$ of L pertains to one operating condition $o_k$ and, as a result, can be calculated from the results $\mu=\{\mu_i, i=1 \ldots N_M\}$ of one experiment. The entire matrix L can be computed from No experiments. That is, one experiment is performed for each of the operating variables as follows:

$$\{L_{ik}, i=1 \ldots N_M\} \cong \{\mu_i, i=1 \ldots N_M\}/o_{kk} = \Lambda(o_k)$$

One such experiment consists of changing the temperature from the setup conditions while leaving all other conditions unchanged. This yields the column of L that pertains to temperature as the column vector of measurements (for example a set of phases at various frequencies for this experiment) divided by the change in temperature. The estimate of $L^{-1}$ is then one of any of the estimators known in the art for inverting linear operators. The numerical model for $\Lambda$ in the above procedure requires many physical parameters to be known, e.g., the elastic and thermo-elastic constants and density of silicon. These values may be obtained from scientific and engineering literature; however, it may be advantageous to adjust some of these parameters for use in the present invention so that the numerical model for $\Lambda$ matches experimental results of the measurement system in question. As an alternative to the preferred, linear approximation $L^{-1}$ of $\Lambda^{-1}$, non-linear inverses of $\Lambda$ can also be employed by the present invention. Both types of inverses are encompassed by the following discussions of the present invention herein, which are primarily directed to the preferred linear approximation.

Wafer-by-wafer calibration

To further linearize the operators involved (e.g., $\Lambda$ and its linear version L), or to better condition the inversions (e.g., the matrix $L^{-1}$ used to derive the operating condition from the measurements), it is desirable to remove some operating conditions from the inversion by measuring their effects upon each particular wafer. This is accomplished by making a calibration measurement $M_c$ on each wafer when the active operating condition is known to be $O_c$. As described below, wafer-calibration can be performed using the same or different equipment from that used to capture process measurements M.

When the same equipment is used, the measurement perturbation $\mu=M-M_c$ is related to the operating perturbation $o=O-O_c$. When different equipment is used, the measurement perturbation, shown in (Eq. 0), $$\mu=(M-\kappa M_c)-(M_0-\kappa M_{c0}) \tag{Eq. 0}$$

is related to the operating perturbation $o=(O-O_c)-(O_0-O_{c0})$, where $M_{c0}$ is the measurement on the calibration equipment under setup conditions, and the matrix hardware function K is a correction operator to account for differences between the measurement equipment and the calibration equipment, e.g., the pin spacing.

In the simplest case, temperature is the only operating condition of interest, and the goal of calibration is to remove essentially all other variables from the measurement, e.g., wafer thickness, wafer orientation and structures on the wafer. Because of the linear nature of the inversion described above (i.e., $O \cong L^{-1}\mu+O_0$), this leads to a simplified view of the measurement. For temperature calibration, a temperature $T_{cm}$ is acoustically measured using calibration equipment when the actual temperature is known to be $T_c$. As a result, with identical calibration and process measurement equipment, the actual acoustic temperature $T=T_r-T_{cm}+T_c$, where $T_r$ is a raw acoustic temperature. That is, the correction factor of $T_c-T_{cm}$ is used to correct process measurements to reflect wafer-to-wafer differences.

In the preferred embodiment, the correction factors for all wafers being processed are stored in a calibration database 144 (FIG. 3A) so that appropriate corrections can be made as multiple wafers are processed and characterized with the different measurement equipment. In more general situations, the calibration measurement, the calibration operating condition, setup values, setup measurements and hardware functions, or functions thereof, are made available to a processing module (FIG. 3A) to enable the processing module to obtain an absolute characterization of the wafer.

Key goals in choosing the venue for calibration include knowing the temperature at the calibration venue and delaying wafer processing as little as possible. For example, a process chamber might be a convenient site for calibration wherein the wafer is calibrated upon entering the chamber. However, in a typical process a wafer enters the chamber shortly after the previous process has been completed when the chamber temperature is high but cooling. As a result, upon entering the chamber, the wafer would likely heat rapidly, providing unsatisfactory calibration measurements. The present invention includes several possible implementations for wafer-by-wafer calibration that satisfy these key goals. These embodiments are described below, following a description of a wafer processing environment in which the present invention can be implemented.

Preferred System Configuration

Referring to FIG. 2, there is shown a schematic diagram of a processing cluster 110 that includes multiple processing chambers 112, each of which can be configured to perform one or more wafer processing steps (e.g., deposition, annealing, etching, etc.). The processing cluster 110 also includes additional stations used for auxiliary processing functions, including a transfer chamber 111, orienters 114, load locks 116 and cool down stations 118. Wafers are loaded into the cluster 110 at one of the load locks 116, can be oriented for subsequent processing by the orienter 114 and are then moved through one or more of the processing chambers 112 to be processed. At the completion of processing, the wafers can be moved to the cool down station 118. These aspects of the processing cluster 110 are typical.

The present invention provides measurement and control apparatus that interact with the wafers as they are being processed in the cluster 110. Through this interaction the wafers can be characterized according to the perturbation techniques described above. A preferred embodiment of the wafer characterization system of the present invention as implemented in a process chamber 112 is now described in reference to FIG. 3A.

Referring to FIG. 3A, there is shown a schematic diagram of a processing chamber 112 and some of the elements of the present invention with which it interacts. This diagram is equally applicable to the implementation of the present invention in the auxiliary chambers 111, 114, 116, 118. The chamber 112 includes a wafer 122 and a chuck 124 that supports the wafer 122 during processing. As described in reference to FIG. 1, the present invention employs pin transducers 128 (the single pin transducer 128 shown in FIG. 3A represents one or more pin transducers) in contact with the wafer 122 to make the various measurements required to determine calibration and processing conditions. As a result, the chuck 124 is configured to allow the pins 128 to contact the back of the wafer 122.

In a preferred embodiment the chuck 124 includes through holes or other through structures to allow the pins 128 to contact the wafer 122. Preferably, the side of the chuck that contacts the wafer includes vias defined therein. The geometry of these vias is defined by the locations of the transmitting pin and the receiving pins so that acoustic energy from the Lamb waves propagating in the substrate between the transmitting pin and the receiving pins is not coupled to the chuck. This reduces the likelihood that the process values computed for the characteristic(s) of interest are influenced by acoustic properties of the chuck.

Referring to FIG. 3B, there is shown a wafer-side view of a preferred embodiment of the chuck 124. During processing, the wafer 122 (whose position is indicated by the dashed line) is in contact with the side of the chuck shown in FIG. 3B. An elliptical "via" 124.1 is defined in the chuck 124. The two foci of the elliptical via 124.1 correspond to the placements of transmitter and receiver pins 125.1, 125.2. The elliptical shape of the via 124.1 ensures that acoustic properties of the chuck 124 will not interfere with acoustic measurements on the wafer 122 in a meaningful way. For example, because the chuck 124 is not in contact with the wafer 122 in the region of the via 124.1, acoustic waves traveling in the wafer 122 between the points 125.1, 125.2 are only affected by the properties of the wafer 122. Moreover, due to the elliptical shape of the via 124.1, any acoustic reflections in the wafer from outside the via 124.1 will arrive at the receiver either after some well-defined time, when they are easily removed through signal processing operations, or with negligibly low amplitude. A three-dimensional view of the same chuck 124 is shown in FIG. 3C.

In cases where the wafer cannot remain unsupported over so large a region, it can be supported in a number of places within the via, whose combined area is significantly less than that of the street itself.

FIGS. 3B and 3C show just one preferred embodiment of a chuck for acoustic characterization of wafers. Different embodiments consistent with the teachings of he present invention can also be designed based on the particular measurement geometry employed and the processing steps involved. Each chuck design should satisfy at least some of the following criteria:

(1) support the wafer as needed;
(2) reduce acoustic interaction between the wafer and the chuck in regions where the wafer is being characterized; and
(3) not cause spurious acoustic waves in the wafer that would be difficult or impossible to filter out when the desired acoustic waves are analyzed.

Referring to FIG. 3A, the chamber 112 is coupled to a corresponding hardware/processing set that includes front end electronics 130 and/or a pulser 132, an acquisition module 134 and a processing module 140. When a pin transducer 128 is used as a transmitter it is excited by the pulser 132, which applies a high voltage pulse 133 to the pin's sourcing transducer. In the preferred embodiment, activation of the pulser 132 is controlled by the acquisition module 134.

The front end electronics 130 amplify the analog electrical signals 129 generated by respective pins' transducer elements in response to acoustic signals that have traveled down the pins 128 (i.e., away from the wafer 122). As described in reference to FIG. 1, when a pin transducer 128 is a transmitter the signal 129 is an echo due to reflection of energy propagating up the pin; when a pin 128 is a receiver it is due to the arrival at the pin's probe end of a Lamb wave transmitted across the wafer 122. The front end electronics 130 are disabled during and shortly after the issuance of a pulse 133 to prevent damage to the pre-amplifiers resulting from the high excitation voltage. The front end electronics 130 output amplified analog signals 131 to the acquisition module 134, which digitizes and filters the signals 131 and outputs the resulting digital signals 135 to the processing module 140. The acquisition module 134 can be flexibly multiplexed to perform acquisition operations for any number of the chambers 111, 112, 114, 116, 118 or for a single chamber as shown.

The processing module 140 coordinates the operations of one or more of the acquisition modules 134 associated with the process chambers 112 and auxiliary chambers 111, 114, 116, 118 for the cluster 110. The processing module 140 also receives from one or more of the acquisition modules 134 a set of digital signals 135 from each of the chambers 111–118 that is providing wafer characterization information in accordance with the present invention. The processing module 140 includes at least a processing unit ($\mu$P) 136 and a memory 142 that can be any combination of fast semiconductor memory (such as RAM or ROM) or slower magnetic memory (such as a hard disk drive). Using the signals 135, the processor 136 performs the computations described above to determine the operating condition O of the wafer from measurements M (corresponding to the digital signals 135). The memory 142 can be used to store a database 144 of calibration values $O_c$ and measurements $M_c$ recorded for individual wafers, hardware functions ($\kappa$) 146 used for computations, a characterization sensitivity ($\Lambda^{-1}$ or $L^{-1}$) 148 that relates measurement perturbations $\mu$ to operating condition perturbations o, a database 145 of setup values $O_0$ and measurements $M_0$ stored for individual wafers, a results database 147 storing characterization results for the individual wafers, and programs 150 that can be executed within the processor 136 to control the various processor operations. The programs 150 typically include processing programs, measurement programs and operating system routines. Faster parts of the memory 142 are used during program execution in the conventional manner. The processing module 140 can be connected to a user interface/display unit 152 to allow users to monitor and control the activities of the processing module 140.

Having described the generic processing environment in which a preferred embodiment of the present invention is implemented, different system embodiments that can perform calibration and/or subsequent measurements are now described with respect to FIGS. 4–6. Many of these embodiments refer to the acquisition module 134 and processing module 140 of FIGS. 2 and 3A. Note that the teachings of the present invention are not limited to embodiments that include discrete components whose functions correspond exactly to these modules 134, 140, but apply to any combination of processing/control elements that perform the functions, operations and/or calculations described herein. Additionally, multiplexer features an be employed that enable any number of acquisition modules to interact with any umber of processing modules and/or chambers 112–118.

Calibration station

The temperature in the auxiliary chambers 111, 114, 116, 118 (FIG. 2) is more likely to be well known than that in the process chamber(s) 112, meaning that the auxiliary chambers are likely candidates for calibration stations. In particular, the transfer chamber 111, orienters 114 and cool-down chambers 118 are attractive candidates for calibration stations as they would allow the calibration temperature $T_c$ to be at room temperature.

Referring to FIG. 4, there is shown a schematic diagram of an orienter 114 configured as a calibration station. Before or after the orienter 114 has done its traditional job, the acoustic pins 128 are used to contact the wafer 122 and make the calibration measurement. Any of the other auxiliary stations 111, 116, 118 could be used in this fashion as long as they are configured to allow the pins 128 to contact the wafer 122.

Acoustic lift pins

Referring to FIGS. 5A and 5B, there are shown illustrations of an alternate embodiment of a calibration system implemented in a process chamber 112. In many process chambers, the wafer is set on lift pins 162 immediately after it has entered the process chamber 112. In this embodiment two (or more) of these lift pins (e.g., the pins 162-1, 162-2) are acoustically active in accordance with the present invention. As soon as the pins 162 are supporting the wafer 122 they collect acoustic data for a calibration temperature $T_c$ at the known/assumed entry temperature (FIG. 5A). The time it takes for the wafer to be lowered (while being supported by the pins 162) into the process position on the chuck 164 is generally sufficient for the calibration measurement to be made (FIG. 5B). As a result, this embodiment requires no additional process steps or time.

If the lift pins 162 are allowed to touch the wafer during processing of the wafer, they could also serve as the acoustic pins 128 (FIG. 3A) for measuring process temperatures.

Pre-chuck calibration position.

Referring to FIG. 6A, there is shown another calibration system embodiment for use in a process chamber 112. At the beginning of the process, when the lift pins 162 are lowering the wafer towards the chuck 164, the acoustic pins 128 protrude above the chuck surface 168 so that they, rather than the chuck 164, receive the wafer 122 from the lift pins 162. The wafer 122 remains unchucked (Oust above the chuck surface) for several seconds while the pins 128 make the calibration measurements. Then the wafer is lowered to the chuck, and these same acoustic pins 128 can be used during the process to measure temperature.

The pins 128 can be actuated (FIG. 6B) or passive (FIG. 6C). Referring to FIG. 6B, the height (h) above the chuck surface 168 of an actuated pin 172 is controlled by an actuator 174. Given this configuration, after making the calibration measurement the actuator 174 lowers the pins 172 and the wafer into process position before activation of the chuck 168. Typically, for a chucked wafer springs 176 between the actuator(s) and pins control the pin force (the force between the wafer and the pin).

Referring to FIG. 6C, a passive pin 182 has no actuator and is supported by a spring 184. When the calibration measurement is being made the springs 184 are uncompressed. Following calibration, activation of the chuck 164 draws the wafer 122 down to the chuck 164, compressing the springs 184. This configuration is mechanically simple and provides controlled pin contact force during processing.

Low-power calibration step

A potential problem with the three previously described calibration implementations is the very low force exerted between the wafer and pins during calibration, when the wafer is not chucked. In contrast, in some cases chucking the wafer requires the use of a plasma that heats the wafer and greatly increases the uncertainty in the wafer's temperature. A resolution of this conflict between pin contact force and determinable wafer temperature is provided by an embodiment illustrated by the flowchart of FIG. 7.

In this embodiment, the power of the plasma is reduced (step 212) after it has been ignited (210) to reduce the heating of the wafer while still allowing chucking (214). While the plasma power is low, with the wafer 122 chucked, an acoustic thermometer implemented in accordance with the teachings of the present invention collects calibration data as already described (216). Following the taking of calibration measurements, the power of the plasma can be adjusted as required for processing (218). As in the previous embodiments, the acoustic thermometer can also take process measurements.

It is now described how the acquisition modules 134 and processing module 140 compute the measurements $\mu$ and corresponding operating conditions o.

B. Phase Estimation/Processing Method

Referring to FIG. 8, there is shown a flow chart indicating the steps of a preferred embodiment for computing the measurements $\mu$ and operating conditions o from a set of acoustic experiments conducted on a test object (e.g., a wafer) using pin transducers configured in accordance with one of many preferred embodiments. These steps are carried out cooperatively by the acquisition and processing modules 134, 140. As already described, the first step involves exciting elastic (e.g., Lamb) waves in a test object and then detecting the elastic waves at respective interrogation points on the test object (step 306). For example, when the pins 3 and 8 are used in the measurement configuration of FIG. 1, the analog signals 131 correspond to the EW(t) and TW(t) signals.

Next, the analog signals 131 are subjected to various analog signal processing operations that, among other things, remove noise, and then are digitized to produce a set of digitized waveforms 135 that can be digitally filtered and then processed in a variety of ways to generate the measurements μ (308). Given the need to estimate particular operating conditions o (e.g., temperature), the type of measurements μ can be chosen to best linearize Λ. In a preferred embodiment μ is chosen to be a set of perturbations of spectral inverse phase velocities squared: $\mu_1 = v_i^{-2}$, where i is the frequency index. As spectral phases of waveforms are the key components in estimating the needed phase velocities, the next step involves performing a Fast Fourier Transform (FFT) on the digitally-filtered waveforms to generate the spectral phase information 311 (310). Given the spectral phases 311, phase velocities v; are computed (400) (recall that, in the preferred embodiment, $\mu_i = v_i^{-2}$). Note that the steps 306, 308, 310 and 400 are performed for setup and calibration conditions, when all characteristics of interest are known and during processing, when at least one of the characteristics is not known.

Then, using the phase velocities v; computed for both setup and processing conditions, the operating conditions are estimated (450). Certain of these steps are now described in detail, starting with the digitization step 308, additional details of which are illustrated in FIG. 9A.

Waveform Digitization

Referring to FIG. 9A, there is shown a data flow diagram illustrating processing elements/operations employed in the digitization step 308. These processing elements include an anti-aliasing filter 330, a digitizer 332, amplifiers 334, an averager 336, notch filters 338 and other analog filters 340. The individual implementation of each of these components/operations is conventional; however, their combination is not. In the preferred embodiment waveform digitization is performed by the acquisition module 134, which embodies the functions/operations described in reference to FIG. 9A. Alternatively, the averager 336 can be implemented either in the acquisition module 134 or the processing module 140. In the latter case the averager 336 is implemented using the existing memory 142 (FIG. 3A) and the microprocessor 136.

An analog waveform 131 is amplified by the amplifiers 334, whose gain ensures that the amplitude of the resulting waveform 335 is less than but nearly equal to the range of the digitizer 332. This gain may be dynamically controlled. The waveform 335 is then operated on by the filters 338, 340.

Noise appears on the signals 131 due to the processing environment in which the measurements μ are made. In particular, the plasma source generator and plasma bias generator (neither are shown), either individually or together, generate noise on the waveforms 131, especially the transmitted waveforms TW(t) (FIG. 1), which have substantially lower amplitudes than the echo waveforms EW(t) (FIG. 1). In some cases, the environmental noise is narrowband, and one or several notch filters 338 may be used to remove it. In other cases the noise may have a broad spectrum which is not white, e.g., weighted more toward lower frequencies, in which case other analog filters 340 may be used to improve the signal to noise ratio, as is known in the art. The noise-filtered signal 339 is then operated on by the anti-aliasing filter 330.

The anti-aliasing filter 330 ensures practical compliance with the Nyquist sampling theorem of the digitization process given the digitization rate of the digitizer 332. I.e., the anti-aliasing filter 330 effectively eliminates components of the analog waveform 339 whose frequencies are greater than one half of the digitization frequency. The output of the anti-aliasing filter 330 is digitized by the digitizer 332 and the resulting digitized signal 333 is passed on to the digital averager 336.

The digital averager 336 then generates the digitized output signal 135 by averaging the signal 333 from the digitizer. The digital averager 336 is for the frequent case where the noise is not synchronous with the ultrasonic signals 131 and can therefore be reduced by waveform averaging.

Details of the digital processing step 310, which is performed on the digitized waveform 135, are now described in reference to FIG. 9B. In the preferred embodiment, these digital processing steps are performed by the processing module 140.

Cycle Subtraction

Referring to FIG. 9B, the digital processing step 310 includes the following operations: cycle subtraction 312, conditioning 314, peak-envelope detection 316, window selection 318, window taper 320, and Fourier phase calculations 322.

In some cases, significant noise may corrupt the digitized waveforms 135. If this noise is nearly cyclical, cycle subtraction (step 312) can reduce it. Cyclical in this case means that the noise has a period and shape within the period that is well defined over the duration of one waveform, but not necessarily over longer time scales. Cycle subtraction estimates one cycle of the noise from a digitized record over a time interval when the signal from the experiment is not present, i.e., before the source is excited, or before the effect of exciting the source has contributed to the waveform in question, and then subtracts that noise cycle from the data over the time interval of interest. The following simple implementation of cycle subtraction illustrates the principle.

For noise with an estimated or known period T, and a waveform digitized at a rate ∂t, a noise cycle consists of $N_n = T/\partial t$ samples. Over a portion of a waveform $W_i^n$ that consists of just noise the estimated noise cycle over $N_c$ cycles is $$w_j^n = \sum_{m=1}^{N_c} w_{j+(m-1)N_n} / N_c.$$

Cycle subtraction yields an estimate of a signal waveform $W_i^s$ from a signal and noise waveform $w_i^{s+n}$ as follows: $w_j^s = w_j^{s+n} - w_{mod(j,N_n)}^n$. In this equation $mod(j, N_n)$ is the remainder of $jIN_n$, $w_i^n$ comes from the time between the excitation of the source and the first acoustic arrival at the receiving element and $w_i^{s+n}$ represents the whole digitized waveform or its portion of interest. In the preferred embodiment cycle subtraction removes noise from all transmitted waveforms. This noise can include acoustic noise set up in the wafer by plasmas used during processing. Various means are known in the art to deal with the more complex situation, when T is not an integral multiple of ∂t, as assumed in the illustration above, or when T is not known a priori.

Conditioning Filter

Referring again to FIG. 9B, the conditioning filter 314, which operates on the output from step 312, consists of some combination of a compression filter 314a, a band-pass filter 314b and a decimation filter 314c. The high pass characteristic of the band-pass filter 314b removes from the input signals any DC offset in the electronics, low-frequency ringing or recovery of the electronics, and out-of-band noise. The low pass characteristic of the band pass filter 314b also removes out-of-band noise. If the cut-off frequency of the low-pass characteristic is sufficiently below the Nyquist rate of the waveforms, the waveforms can be decimated by the filter 314c.

Referring to FIG. 10A, there is shown a plot of an echo waveform EW(t) as it might look upon its input to the signal conditioning step 314. The portion of the signal just after 0 μs is the excitation pulse which was applied to the sourcing element. This portion is distorted by the electronics, which are designed to detect the much smaller-amplitude acoustic signals. The portion of the EW(t) waveform just after 20 μs represents the acoustic echo from the top of the pin. This echo signal is relatively clean and can typically be conditioned using only the bandpass filter 314b and, sometimes, the decimation filter 314c. The signal at 40 μs is a multiple of the echo: it has traversed the length of the pin four times rather than just two. The echo is relatively compact in time, its width being largely controlled by the bandwidth of the transducer formed by the element bonded to the sourcing pin, and therefore does not require compression by the filter 314a.

Referring to FIG. 10B, there is shown a plot of a transmitted waveform TW(t) as it might look upon its input to the signal conditioning step 314. Note that there is no distorted pulse at 0 μs as the transmitted waveform TW(t) is generated by a receiving pin transducer that is separated from the sourcing pin transducer and therefore the excitation pulse. The signal of interest persists from roughly 35 μs to 55 μs. This portion represents the directly transmitted signal which has taken the shortest possible path from the sourcing element to the receiving element. The signal after 55 μs, when high-frequency components suddenly appear and the amplitude begins to grow again, is a "multiple", i.e., the transmitted signal corresponding to the multiple echo discussed above. In general, multiples have propagated over a longer path, and have interacted at least one extra time with the end of the pins or the edge of the wafer. They are generally unwanted signals that are not analyzed further.

The compression filter 314a is especially advantageous for application to transmitted waveforms TW(t), which can be dispersed in time by the variation of the wafer wave's phase velocity v(f) as a function of frequency f. FIG. 11, illustrates, e.g., Lamb wave dispersion for the lowest order antisymmetric Lamb wave (A0) mode, whose velocity increases with frequency. Thus, in FIG. 10B, the high-frequency components of the transmitted waveform TW(t) arrive at the receiving element earlier than low frequency components.

Dispersion causes two practical problems. One problem is cycle skipping when picking a time reference for signal measurements. For example, when using the time of a zero crossing (TOF) as the measurement, as in the prior art, and when it is desired to have an absolute temperature (which was not attempted with the previous art), it is necessary to pick a particular zero crossing. However, zero crossings move in time with respect to the waveform's envelope as functions of the operating conditions, so it is very difficult to pick a particular zero crossing with the dispersed waveform. The second problem relates to spectral estimation, as practiced in the current art. When using the Fourier transform to estimate a spectrum, it is necessary to choose a window in time that includes only the signal of interest. Furthermore, the signal should effectively start after the beginning of the window and die away before the end of the window. Referring to FIG. 10B, it is clear that the desired signal cannot be properly windowed because its low-frequency tail overlaps the high-frequency head of the multiple. Thus, it is advantageous to compress the waveform using the compression filter 314a to allow proper windowing for spectral estimation. This compression operation is now described in reference to FIG. 12.

Referring to FIG. 12, there is shown a flowchart of the steps implemented in the compression filter 314a, which include backpropagation 410 and Wiener filtering 412. The first step in compression 314a is backpropagation 410. In this step, the compression filter 314a calculates, based on the assumption of some reasonable operating conditions, a theoretical estimate of the velocity of the wafer wave $v_c(f)$. The compression filter 314a uses the estimated velocity $v_c(f)$ to determine the frequency response $H_b(f)$ of the backpropagation filter 410 as $H_b(=\exp(i2\pi fz/v_c(f))$, where z is the length of the path 6 (FIG. 1) and the Fourier transform is defined as $F(\cdot)=f\cdot\exp(-i2\pi ft)dt$. Application of the backpropagation filter 410 characterized by $H_b$ to the transmitted waveform TW(t) in FIG. 10B yields the backpropagated waveform $w_b(t)$ shown in FIG. 10C. Note that the backpropagated waveform $w_b(t)$ is more concentrated in time and has less overlap with the following multiple than the transmitted waveform TW(t).

The Wiener filtering step 412 further improves the results of the compression filter 314a beyond the capabilities of simple backpropagation 410. The goal of the Wiener filter 412 is to make the portion of the backpropagated waveform $W_b(t)$ between asterisks (designated $w_p(t)$ on FIG. 10C), look as much as possible like a target waveform $w_t(t)$ (FIG. 10D). The amplitude spectrum of the target waveform $w_t(t)$ should be similar to that of the original transmitted waveform (shown in FIG. 10E) in order to avoid noise artifacts and yet maintain a short signal duration. The phase of the target waveform $w_t(t)$ should produce a compact pulse. In the preferred embodiment, the target waveform is the impulse response of a Bessel-type bandpass filter that fulfills these requirements. However, alternative embodiments can employ other filter types that achieve the same or better results than the preferred embodiment.

Given the aforementioned conditions, in the preferred embodiment the first Wiener filter is represented by: $H_{w1}(f)=W_p^*W_t/[|W_p|^2+C]$, where W=F(w) (i.e., W is the Fourier transform of w) and C is a factor (the constant (0.001 max($|W_p|^2$) in the preferred embodiment) that gives filter stability. As illustrated in FIG. 12, the Wiener filter step 412 could be iterated multiple times to arrive at the final Wiener filter. Each iteration includes the following conventional steps:

(1) select a portion of the waveform from which to calculate the Wiener filter;

(2) calculate the Wiener filter;

(3) apply the Wiener filter to the whole waveform; and (4) repeat step (1); or (5) output the Wiener filter calculated in step (2) as the final Wiener filter.

In the preferred embodiment the Wiener filtering step 412 is iterated once, resulting in two Wiener filters $H_{w1}(f)$ and $H_{w2}(f)$.

The compression filter $H_{comp}(f)$ is the product of the back-propagation filter $H_b(t)$ and any computed Wiener filters $H_{wi}(f)$ and can be represented as $H_{comp}(f)=H_b\pi_{i=1}^{N_w}H_{wi}$, where $N_w$ is the number of Wiener filters (2 in the preferred embodiment).

The result $w_c(t)$ of applying the compression filter 314a (including the Wiener filtering 412) to the original transmitted waveform TW(t) is very compact, as seen in FIG. 10F. The compression filtering has shifted the time axis so that the signal of interest now occurs at roughly the origin. This is an incidental effect of the procedure described above, and is not a problem for the steps which follow, since they concentrate on phase or time differences between waveforms that have been processed with the identical filter. Specific zero-crossings, or indeed, other features, such as peaks, are easily identified. Further, separating the desired signal from multiples with a window is also easy. The compression filter 314a, and all other filters 314b, 314c discussed up to this point are chosen as part of the setup procedure and fixed at that time. During the measurement of temperature, exactly the same filters are applied to each digitized transmitted or echo waveform.

Windowing

Referring again to FIG. 9B, windowing steps 316–320 are performed on the results of the compression step 314 to select for further processing only those portions of the waveforms that are of interest. Windowing is a well known digital signal processing procedure in which a symmetrical, smoothly tapering function (called an apodization or shading or tapering) is applied to the portion of a compressed waveform selected for fast Fourier transforming (FFT). The time extent of the apodization determines the size of the FFT window and the tapered shape of the apodization function ensures that the argument of the FFT tapers smoothly to zero at the edges of its domain.

It is desirable that the placement of the window and apodization with respect to the signal of interest be as repeatable as possible. Thus, the first windowing step 316 involves detecting a feature of the compressed waveform $w_c(t)$ that serves as a reference for positioning the apodized window. The variation in the delay of the compressed waveform makes dynamic positioning of the window advantagous. However, the change in shape of the compressed waveform due to variation in the temperature, thickness, and other operating conditions of the wafer under test make repeatable positioning difficult. The shape of the waveform can change significantly, e.g., due to the strong dispersion of the Lamb wave (FIG. 11). The peak of the envelope of the compressed waveform, over some preselected range in time, is a recognizable signal feature that is used by the preferred embodiment to determine the placement of the apodized window, as shown in FIG. 13A.

Referring to FIG. 13A, there is shown a plot of the compressed waveform w(t) (i.e., the waveform produced by step 314) and its corresponding "analytic signal" (the dark line overlaying the waveform trace). As is known in the art, the analytic signal is a broadband envelope calculated as the magnitude of the complex signal whose real part is the original waveform and chose imaginary part is the Hilbert transform of the original waveform: $w(t)=|w(t)+i\mathcal{H}[w(t)]|$, where $\mathcal{H}$ is the Hilbert transform.

Once the envelope peak has been detected, the waveform window is selected in relation to the detected peak (step 318, FIG. 9B). In the preferred embodiment the peak of the analytic signal, denoted by an asterisk (*) in FIG. 13A, is the center of the window whose total duration is 8 $\mu$s, and whose endpoints are denoted by "x".

Once the window has been selected the apodization function a(t) is applied within that window (320). The apodization function can be any of those known in the art. In the preferred embodiment, as shown in FIG. 13B, the apodization function is a half cosine $a(t)=\cos(\pi(t-t_p)/T_a)$, where $T_a$ is the duration of the window and $t_p$ is the time of the peak of the analytic signal. The windowed waveform (the lighter plot in FIG. 13B, which is the product of w(t) and a(t)) is passed to the FFT, which determines the spectral phase of the waveform's frequency components (step 322, FIG. 9B).

Spectral Phase

In step 322 (FIG. 9B) the processing module 140 computes the fast Fourier transform (FFT) of the windowed waveform in the standard manner and then outputs the phase information from the FFT as the spectral phases $\phi(f)$. The phases $\phi(f)$ are given as $\phi(f)=\angle F_{T_0}[w(t)a(t)]$, where $F_{T_0}[\cdot]$ is the fast Fourier Transform over some domain $T_0$ and $\angle$ represents the phase angles of the various frequencies. In this computation phase corrections for changes in the time coordinate and phase unwrapping are implicit. Referring to FIG. 13C, there is shown a plot of the phases $\phi(f)$ computed for the windowed waveform shown in FIG. 13B. Only some of the spectral phases (e.g., those marked with asterisks in FIG. 13C) are retained for measuring the temperature. To improve clarity, the phase in this figure has had a linear phase (with respect to frequency) removed. The same procedure measures the phase of compressed transmitted waveforms and echo waveforms. Thus, at the completion of step 322, the spectral phases $\phi(f)$ are available to be used as a measurement perturbation $\mu$ needed to derive the operating condition perturbation o.

Having described how the spectral phases 311 are computed, details of the step 400 (FIG. 8), in which phase velocities are computed from the spectral phases 311, are now described.

C. Velocity Estimation

There are candidates for the measurement M that yield a more linear relationship between the measurement perturbation $\mu$ and the operating perturbation o than the spectral phases $\phi(f)$. One possible candidate is the inverse square of the Lamb-wave velocity of the wafer, $1/v^2$, which can be calculated from the phases $\phi(f)$. The velocity v is implicitly a function of frequency over some range of frequency. The theoretical model underlying wave velocity measurements and preferred embodiments that employ wave velocity measurements to estimate the operating conditions are now described for the SET configuration described in reference to FIG. 1. These results are generalizable to different measurement configurations.

Theoretical model

A spectral representation of the waveforms EW(t) and TW(t) (FIG. 1) yields a model for the velocity calculation. The spectrum of the echo waveform EW(t) in the sourcing pin (e.g., pin 3 in FIG. 1) can be represented as: $W_{E1}=\eta_0\eta_1^2\exp(2i\phi_{p1})\psi_1$, where all quantities except explicit constants are functions of frequency. In particular, $\eta_1$ is the sourcing efficiency of the sourcing transducer (i.e., the combination of the sourcing element and pin), $\eta_0$ is a reciprocity factor that relates sourcing to receiving efficiency, $\phi_{p1}$ is the one-way propagation phase in the sourcing pin and $\psi_1$ is the complex reflection coefficient at the boundary between the sourcing pin and the wafer (e.g., the wafer 1 in FIG. 1).

The spectrum of an echo waveform $EW_2(t)$ in the receiving pin (e.g., pin 8 in FIG. 1) can be represented similarly: $W_{E2}=\eta_0\eta_2^2\exp(2i\phi_{p2})\psi_2$, where parameters associated with the receiving pin are designated by the subscript 2. The echo waveform $EW_2(t)$ is not used in the SET geometry described in reference to FIG. 1, but it is used in a dual echo, single transmitter (DET) geometry. The DET geometry provides better characterization results than the SET geometry as the additional echo waveform $EW_2(t)$ accurately indicates the wave velocity in the receiving pin (in the SET geometry, this is estimated from the echo measurement in the sourcing pin). However, one additional complexity in the DET geometry is that the echo in the receiving pin must be excited. The DET geometry is described in greater detail below.

The spectrum of the transmitted waveform TW(t) can be represented as: $W_T=72\ _0\eta_1\exp(i(\phi_{p1}+\phi_{p2}+\phi_D))\xi_{1L}\xi_{L2}\zeta$, where $\phi_D$ is the phase of a plane (i.e., with linear wave fronts) Lamb wave (note: in the present document, the term "Lamb wave" encompasses all relevant substrate wave types) propagating directly from the sourcing pin to the receiving pin, $\xi_{1L}$ is the transmission coefficient from the wave in the sourcing pin to the Lamb wave in the plate, $\xi_{L2}$ is the transmission coefficient for the Lamb wave to the wave in the receiving pin and $\zeta$ is a diffraction correction that accounts for the difference between the actual cylindrically expanding Lamb wave and a plane Lamb wave. The procedure used by the processing module 140 to compute the Lamb wave velocity is now described in reference to FIG. 14.

Phase Perturbations

Referring to FIG. 14, there is shown a flow chart illustrating the steps performed by the processing module 140 to compute the measurement perturbation.

The interpretation of FIG. 14 and the following descriptions depend on the calibration strategy, where "calibration" means wafer specific calibration. If there is no calibration the setup hardware description is as it appears. If the same hardware is used for calibration and process measurements, the calibration phase perturbation must be calculated and used in conjunction with the process phase perturbation, as described in Eq. (0).

In the preferred embodiment a calibration operation 358 (described above in reference to FIGS. 4–7) is performed on each wafer to be characterized. In this calibration operation the phase or velocity of at least a transmitted waveform is determined for known operating conditions (e.g., any combination of wafer thickness, wafer temperature and wafer film thickness). The results of each calibration measurement are stored in the calibration database 144 (FIG. 3A) for each wafer to be characterized. Alternatively, when a particular wafer to be characterized has not been calibrated, experimental or estimated results can be used. In this case, the alternate calibration values are also stored in the calibration database 144. In some situations where the calibration configuration is the same as the setup configuration, the calibration and setup measurements are equivalent, in which case it is not necessary to do both measurements.

The setup echo and setup transmitted waveforms $EW(t_0)$, $TW(t_0)$ are acquired with known operating conditions; i.e., when the perturbations are defined to be zero. Setup quantities are identified herein with an additional 0 subscript. In the preferred embodiment, the setup echo and transmitted waveform measurements are stored in the setup database 145 (FIG. 3A) so they can be selectively accessed by the processing module 140 for each wafer being characterized. The measured echo and transmitted waveforms are then acquired for unknown operating conditions. Once the waveforms are acquired, the procedure for the phase calculation described above is used in each of the four steps 360, 362, 366, 368 to compute the phase information for each respective waveform. However, different respective filters and other parametric choices can be used for the echo and transmitted waveforms. Given the phase measurements computed in steps 360, 362, 366, 368, the perturbation of respective echo and transmitted phases are computed in steps 364 and 370.

For the purposes of the present discussion, the perturbation operator $\Delta[\cdot]$ signifies the difference (i.e., perturbation) between a measured quantity and its setup value. For example, the expression $\Delta[\angle W_{E1}] = \angle W_{E1} - \angle W_{E10}$ gives the perturbation in the phase of the transmitted echo computed at step 364 (note: $W_{E1}$ represents the transmitted echo measurement made during the process and $W_{E10}$ represents the setup transmitted echo measurement). Similarly, the difference of the phases of the setup and measured transmitted waveforms computed at step 370 gives the transmitted phase perturbation $\Delta[\angle W_T]$. Perturbations are computed the same way for either of the receiving and sourcing echo waveforms $EW(t)$, $EW_2(t)$.

The method employed by the present invention to compute Lamb wave velocity assumes that the difference between the transmitted and echo phase perturbations is a close approximation to the phase of the Lamb wave propagating between the two pins, which approximation is represented in Eq. (1).

$$\Delta[\angle W_T - \angle W_{E1}] \cong \Delta[\phi_L] \qquad \text{Eq. (1)}$$

Thus, in the preferred embodiment the Lamb wave phase perturbation is derived (step 372) from the echo and transmitted phase perturbations computed in steps 364 and 370. The validity of this approximation depends in turn on the validity of each of a set of assumptions. Theoretical arguments supporting the validity of the fundamental approximations are now described for the measurement geometry of FIG. 1, which is called the SET configuration (short for Single Echo signal with at least one Transmitted signal). Similar theoretical arguments can be made in support of alternate preferred measurement geometries, which are described below. In general, these alternate embodiments exhibit a better relationship between the phase and velocity perturbations under different conditions than the SET configuration as they require fewer assumptions.

The first assumption is shown in Eq (2).

$$(\angle \eta_2 - \angle \eta_1) - (\angle \eta_{20} - \angle \eta_{10}) \cong 0 \qquad \text{Eq. (2)}$$

This assumption is true for the SET configuration if either (a) neither transducer changed its characteristics between the setup and measurement, or (b) if both transducers changed in the same manner. The first possibility is likely to be true if the sourcing and receiving piezoelectric transducers are maintained at a constant temperature. If this is not the case, the changes in the transducers are likely to track to some extent. Equation (2) is vital to achieving the desired result in Eq. (1). Equation (2) says that the properties of the transducers are not a part of the desired measurement that is supposed to characterize only the wafer. This is one reason for using a setup approach with the perturbation operator: it removes the transducers from the measurement, as represented by Eq. (2).

The second assumption (shown in Eq. (3)) is that the phase perturbations in the two pins cancel.

$$\Delta[\phi_{p1} - \phi_{p2}] = 0 \qquad \text{Eq. (3)}$$

Subtracting the setup values removes gross differences of the pins from the measurement. However, it is not reasonable to assume that the phase perturbations themselves are zero as there will inevitably be some heating of the pins by conduction due to the heating of the wafer. Heating of the pins perturbs their phase velocity in much the same way as heating of the wafer makes the current measurement possible. Thus, this approximation largely reduces to the assumption that the sourcing and receiving pins are heated to the same extent with respect to the setup conditions. This may not be true due to differences in wafer temperature at the respective pins' locations or in the thermal conductivity of the two contacts between the pin and the wafer, e.g., due to interfering particles or a difference in force applied to the pins. Also, if the pins are held in different thermal environments, their heating responses may differ.

The third assumption (shown in Eq. (4)) presumes that the phases of the reflection and transmission coefficients at the pin/wafer interfaces either do not change, or change in synchrony.

$$\Delta[\angle\xi_{1L}+\angle\xi_{L2}-\angle\psi_1]=0 \qquad \text{Eq. (4)}$$

Because of the small linear dimensions of the interface, these coefficients do not contribute much to the total phase; as a result it is likely that small perturbations to the conditions will produce negligible changes via this path. Again, the $\Delta$ operator associated with setup removes the gross characteristics of the interface coefficients from the measurement.

The fourth assumption (shown in Eq. (5)) assumes that the diffraction-induced phase does not change significantly.

$$\Delta[\angle\zeta]=0 \qquad \text{Eq. (5)}$$

The setup $\Delta$ operator removes the gross effects of diffraction from the measurement. Again, because the diffraction correction itself has such a small value, its perturbations are likely to be negligible. Alternative embodiments that reduce the number of approximations, or which improve them, are now described.

Two-echo variation (DET)

An improvement in the estimation of the Lamb phase can be implemented within the measurement geometry of FIG. 1 by recording an echo $EW_2(t)$ at the receiving transducer 9. Since there is normally not an echo at this pin, the electronics must produce one by exciting the receiving transducer as if it were a sourcing transducer. In this case, the term $\Delta|\angle W_{E1}|$ in Eq. (1) is replaced by the term $\Delta[\angle W_{E1}+\angle W_{E2}]/2$.

This modification of the basic measurement essentially makes Eq. (3) exactly true; i.e., no longer an assumption. Additionally, in this configuration the assumption defined in Eq. (4) is replaced by the expression shown in Eq. (6).

$$\Delta[\angle\xi_{1L}+\angle\xi_{L2}-\angle\psi_1/2-\angle\psi_2/2]=0. \qquad \text{Eq. (6)}$$

Velocity estimation

Given a measurement of the perturbation in the Lamb wave phase from setup conditions, and assuming that the Lamb phase is essentially exponential (i.e., that the phase change in radians of a Lamb wave after traveling a distance z can be represented as $\phi=2\pi fz/v$), the measured phase perturbation from step 372 can be represented as shown in Eq. (7), where $v_0$ represents the Lamb wave velocity for the setup condition and z represents the path traveled by the Lamb wave between a sourcing pin and a receiving pin; v and $v_0$ are generally functions of frequency.

$$\Delta[\phi_L]=-2\pi fz(1/v-1/v_0) \qquad \text{Eq. (7)}$$

Through simple rearrangement of Eq. (7), the Lamb wave velocity can be determined according to Eq. (8).

$$v = \frac{-2\pi fz}{\Delta[\phi_L] - 2\pi fz/v_o} \qquad \text{Eq. (8)}$$

The value of the setup velocity $v_0$ can be measured with the system described. However, as it is difficult to measure $v_0$ directly, in the preferred embodiment $v_0$ is calculated theoretically (step 374, FIG. 14). Given the velocities $v_0$ and v, a preferred measurement perturbation is represented as $\mu=\Delta[M]=\Delta[v^{-2}]=v^{-2}-v_0^{-2}$. As above, given the measurement perturbation, the operating condition perturbation can be determined using the aforementioned methods. Other powers of the velocity can be used as the measurement, as well as functions of phase, other spectral quantities, or time-domain quantities such as the times of zero crossings.

D. Edge-Bounce

In some cases it is highly desirable that the region of integration for the average temperature from the measurement includes the edge of the wafer. When using only the direct arrival of the Lamb wave, as in the SET method described above in reference to FIG. 1, the average temperature cannot include the edge of the wafer unless a pin is placed at the edge of the wafer, which is an undesirable placement in many applications. One solution is to use an edge-bounce in the measurement of temperature. In this technique, the Lamb wave is preferably processed twice at a given pin, once in a direct measurement (as in the SET method) and once after it has been reflected from the edge of the wafer.

Referring to FIG. 15, there is shown a schematic illustration of an embodiment that makes use of an edge bounce measurement. The structural elements of this embodiment are similar to that of FIG. 1. That is, in this embodiment the temperature or other characteristic of a wafer 1 is determined using a sourcing (i.e., transmitting) pin transducer comprising a sourcing pin 3 and transducer 2 and a receiving pin transducer comprising a receiving pin 8 and transducer 9. A Lamb wave is set up in the wafer 1 in response to an acoustic wave 4 excited in the sourcing pin 3 by the sourcing transducer 2 (as with all of the embodiments described herein, sources and receivers that are not pin transducers can also be employed). The transmitted edge bounce defined by the paths 11 and 12 in FIG. 15 can be used to provide a measurement of the temperature that is an average of the temperature between the pin 8 and the edge of the wafer 13. In order to achieve such a measurement in practice, the time delay associated with the difference between the paths 11 and 6 (the direct path between the pins 3 and 8—FIG. 1) must satisfy two conditions:

(1) it must be long enough that the directly transmitted waveform arising from paths 6 and 7 does not overlap significantly in time the edge-bounce transmitted waveform arising from paths 11 and 12, and (2) it must be short enough that the edge-bounce transmitted waveform does not significantly overlap with later multiple edge bounces or ohter signals after application of the compression filter. For example, referring to FIG. 10F, a useful edge bounce could occur between roughly 5 and 15 $\mu$s.

The processing for the edge-bounce geometry is a variation of that used for the SET configuration. Two waveforms are processed, the direct transmitted waveform (discussed above) and the edge-bounce waveform, whose spectrum is represented as $W_{EB}=\eta_0\eta_1\eta_2\exp(i(\phi_{p1}+\phi_{p2}+\phi_{EB}))\xi_{1L}\xi_{L2}\zeta_{EB}\psi_{EB}$, where $\phi_{EB}$ is the Lamb-wave phase for the edge-bounce path, $\zeta_{EB}$ is the diffraction correction factor that includes some 'focusing' due to reflection from the circular edge of the wafer, and $\psi_{EB}$ is the reflection coefficient for the Lamb wave from the edge of the wafer. In this case, the fundamental phase perturbation in Eq. (1) is replaced by Eq. (9) so that the edge bounce signal is compared to the directly transmitted signal.

$$\Delta[\angle W_{EB}-\angle W_T]\approx\Delta[\phi_L] \qquad \text{Eq. (9)}$$

This removes the need for the assumptions of Eqs. (2)–(4), but new assumptions (shown in Eqs. (10) and (11)) are necessary, as analogs to Eq. (5).

$$\Delta[\angle\psi_{EB}]=0 \qquad \text{Eq. (10)}$$

$$\Delta[\angle\zeta_{EB}-\angle\zeta]=0 \qquad \text{Eq. (11)}$$

The distance z in Eq. (7), which gives the Lamb wave velocity for the SET configuration, is replaced for this geometry by $z_{EB}$–z, which represents the distance of path 11 in FIG. 15. There are other edge-bounce pulses besides the one pictured above which can be used in the same way, depending on the positioning of the pins. Thus, two carefully-positioned pins used to make both edge-bounce and direct-path measurements can provide average measurements of the operation conditions (e.g., temperature) over two or more zones on the wafer.

E. Multiple Zones

Referring to FIG. 16, there is shown a schematic overhead view of a preferred embodiment of at least two pins wherein edge bounce measurements are employed to map an operating condition of interest (e.g., temperature, film thickness) over a larger collection of radii than is possible with the prior art (which does not employ edge bounce measurements). In FIG. 16, the wafer 1 is contacted by a sourcing pin at point 21 and by receiving pins at points 22 and 24. The center of the wafer 1 is at point 23. In the illustrated embodiment the sourcing pin excites Lamb waves at point 21 that propagate to and are received at points 22 and 24. An additional edge bounce 27 from the wafers edge 13 is also received at point 24. In some cases it will be advantageous to compare some other transmitted wave to the edge bounce, e.g., an echo, as in the SET geometry, or the directly transmitted waveform on another pin. Pins located along a diameter of the wafer, as shown in FIG. 16, are particularly advantageous, especially if the operating conditions are (known or assumed to be) azimuthally invariant about the center of the wafer, e.g., $T(r,\theta)=T(r)$, where r is radial distance on the wafer, and $\theta$ is angular position. To a reasonable level of accuracy, the temperature measured by the acoustic thermometer is $$\bar{T} = \int_S T(r) ds,$$

where S is acoustic path involved in the measurement.

Pins on a diameter have some properties that simplify interpretation of the results in such cases. First, the paths S between any adjacent pins do not overlap. Second, the path for an edge bounce using an outermost pin (e.g., the pin 24), does not overlap any of the other paths. Third, one edge bounce and one or more direct paths cover the full range of radii on the wafer. Finally, diametric positions for the sourcing and receiving pins optimize the acoustic delays when the following challenges are met:

(1) placing the receiving pin sufficiently close to the edge of the wafer to monitor temperatures at the edge of the wafer, and (2) simultaneously separating the direct transmitted waveform from the edge-bounce waveform in time. The separation in time is proportional to the difference between the direct path length and the edge-bounce path length.

Edge-bounce paths are determined by Fermat's principle, which states that the acoustic waves traveling between two pins via the edge of a wafer will follow a stationary path that has either a minimum or maximum delay. For example, for the pin locations 341 and 342 shown in FIG. 17A there are two edge-bounce paths 348A and 348B between those pins. FIG. 17B shows the path lengths between the points 341 and 342 for all points on the edge of the wafer as a function of their angle, where zero angle is at 3 o'clock, and increasing angles correspond to counterclockwise rotation. Stationary points 352A and 352B (marked with asterisks) are those where the delay is not changing, i.e., the derivative of the delay with respect to angle is zero at these points. The only two such points on FIG. 17B correspond to the edge positions 344 and 346 (FIG. 17A), which respectively give rise to the maximum and minimum length paths 348A and 348B (FIG. 17A). On an anisotropic silicon wafer, delays must be calcaulated by the appropriate velocity at a given frequency, known in the art as group, velocity. The examples here use an isotropic approximation that the velocity is 1 mm/14 $\mu$sec regardless of propagation direction.

Referring to FIG. 18A, there is depicted an illustration of the shortest edge-bounce paths between one pin 402 in a fixed location 12.7 mm from the edge of the wafer, and a roving pin 404 at different locations marked by plus symbols "+". The coordinate system in FIG. 18A has been rotated so that the fixed pin 402 lies on the horizontal diameter, without loss of generality. The positions of the roving pin 404 lie on a circle 25.4 mm from the edge of the wafer. Which pin is the source does not matter. The direct paths are obvious, and not shown. Later edge-bounce arrivals are not shown. FIG. 18B is a plot of the difference between the direct and echo paths for the various pin positions 404. The diametric positions, i.e., at 0° and 180°, have the longest delays and are thus best for edge bounce applications. This is true for pins at other radii than the two illustrated here.

In a preferred embodiment, the pin 21 in FIG. 16 is the transmitter. The pin 22 is the "primary receiver". The locations of these pins are chosen to ensure the transmitted pulse is very well separated from any others, so that the inverted temperature can be of the highest quality. The position of the pin 24, the "edge receiver", reflects a tradeoff between the need to measure the temperature close to the edge of the wafer and the need to separate pulses. The quality of the temperature measurement from the edge-bounce may be compromised by this tradeoff. Quality can be further reduced by any uncertainty in the placement of the wafer, which leads to uncertainty in the path length of the edge bounce. For these reasons, it is preferred to treat the edge bounce temperature as a relative measurement. If at some time $t_0$ it is known that the temperature on the wafer is uniform, then the edge-bounce temperature $T_{EB}$ can be 'corrected' by the primary temperature $T_P$ measurement as shown Eq. (12).

$$T_{EBC}(t)=T_{EB}(t)-T_{EB}(t_0)+T_P(t_0) \qquad \text{Eq. (12a)}$$

This is only applicable if temperature is the only characteristic of interest. More generally, where temperature is not the only characteristic of interest, one must use the expressions in Eqs. (12b) and (12c):

$$\mu_{EBC}(t)=M_{EB}(t)-M_{EB}(t_0) \qquad \text{Eq. (12b)}$$

$$O_0=O(t_0) \qquad \text{Eq. (12c)}$$

In order to complete the coverage of wafer radii within a measurement, a secondary temperature $T_s$ can be measured with the direct path from the pin 21 to the pin 24.

F. Multiple Receiver Geometries

The present invention also incorporates embodiments that employ multiple receiving pins to record the arrival of Lamb waves excited by one or two transmitting pins. The first of these multiple receiver geometries, which includes one transmitting pin, is described in reference to FIG. 19. The second multiple receiver geometry, which employs two transmitting pins, is then described in reference to FIG. 20.

Differential Receiver Pair (with One Source)

Referring to FIG. 19, there is shown a schematic illustration of a differential receiver pair (DRP) measurement configuration. In this embodiment there is a sourcing transducer 21 and two receiving transducers 24, 27. The source transducer 21 operates as in the two-pin embodiments already described except that its echo waveform is not used. The receiving transducer 24 also operates in the same manner as in the two-pin geometries; i.e., it detects the expanding circular Lamb wave after it has propagated the distance of the direct path 23, with the resulting spectrum: $W_{T2}=\eta_0\eta_1\eta_2\exp(i(\phi_{p1}+\phi_{p2}+\phi_{D2}))\xi_{1L}\xi_{L2}\zeta_2$, where $\phi_{D2}$ is the phase of a plane Lamb wave propagating directly from the sourcing point 21 to the receiving pin 24 and $\zeta_2$ is a corresponding diffraction correction. The second receiving transducer 27 detects the expanding circular Lamb wave after it has propagated an additional distance along the path 126, with the resulting spectrum: $W_{T3}=\eta_0\eta_1\eta_3\exp(i((\phi_{p1}+\phi_{p3}+\phi_{D3}))\xi_{1L}\xi_{L3}\zeta_3$. The subscript 3 in the preceding expression indicates quantities associated with the receiving transducer 27. With this embodiment the Lamb phase perturbations can be approximated as follows:

$$\Delta[\angle W_{T3}-\angle W_{T2}]\cong[\phi_{D3}-\phi_{D2}].$$

As for the SET embodiment, the validity of this approximation depends in turn on the validity of each of a set of assumptions. Theoretical arguments supporting the validity of the assumptions are now set out; some of the advantages of the DRP configuration over the SET configuration are also described. The main DRP disadvantage is that it requires the use of three transducers rather than two to characterize a wafer over a single zone. Generally, in the present case all effects associated with the sourcing pins, which were a factor in the SET configuration, are moot as the above approximation only involves subtracting the phases from the two receiving pins (with the indices 2 and 3).

As in the SET configuration (Eq. (2)) the first assumption is that $(\angle\eta_2-\angle\eta_1)-(\angle\eta_{20}-\angle\eta_{10})\cong 0$. This assumption holds in the DRP case under the same conditions already described for the SET configuration.

The second assumption is that $\Delta[\phi_{p1}-\phi_{p2}]=0$; i.e., that the phase perturbations in the two pins cancel. This assumption is essentially the same as Eq. (3), which applies for the SET case. For the SET case removal of this assumption requires recording, in addition to the received waveform, the echo on the receiver pin. For the DRP configuration removal of this approximation requires recording an additional two waveforms: the echoes on both receivers 24, 27, if pins are used, as opposed to a laser detector.

The third assumption is that $\Delta[\angle\xi_{1L}+\angle\xi_{L2}-\angle\psi_1]=0$; i.e., that the phases of the reflection and transmission coefficients at the pin/wafer interfaces either do not change, or change in synchrony, which is essentially the same as the corresponding assumption for the SET configuration (Eq. (4)). In the DRP configuration, this assumption is simply true when the pins 24, 27 and wafer contacts are identical. However, in the SET case this assumption is a factor under any and all conditions as Eq. (4) involves determining the difference of quantities (LP and A) that generally have perturbations that are of opposite signs.

The fourth assumption is that $\Delta[\angle\zeta]=0$; i.e., that the diffraction induced phase does not change significantly. As with the preceding assumption, this approximation is likely to be better for the DRP case than for the SET case (Eq. (5)). This is because most of the diffraction correction occurs near the origin of the cylindrical wave; i.e., at the transmitter pin. As a result, there is less diffraction correction for the DRP case than for the SET case and correspondingly smaller perturbations.

A further advantage of the DRP configuration over the two-pin SET methods described above is that it reduces the potential effects of nonlinearity due to large ultrasonic displacements caused in the wafer by the transmitted wave. All of the equations and description up to this point, including the use of spectral phase, assume that the media obey a linear Hooke's law, F=−kx, where F is the force exerted by a spring, x is displacement of the spring and k is the spring constant. This is true as long as the ultrasonic displacements are very small, which may not be the case for the transmitter pin and the wafer in the immediate vicinity of the transmitter pin, where the largest displacements occur. Displacement amplitude is greatly reduced by:

(1) the transmission coefficient from the pin to the wafer, and (2) the spreading of the energy away from the transmitter pin on the wafer.

If the displacements of the transmitter pin and wafer in its vicinity are large enough to cause nonlinearity, this will cause errors in interpreting the results from the SET, but not from the DRP configuration. As mentioned above, the differential receiver pair exactly removes all effects associated with the transmitter pin, since those effects are reflected in the results from both receivers in exactly the same way. Only nonlinearity in the receiver pins themselves or on the wafer in their vicinity or between them will affect the result, which is highly unlikely.

A differential source pair (DSP) configuration, with one receiver and two transmitters, can also be implemented. The theory underlying such a system is similar to that presented above and is therefore not provided herein.

Symmetric Source and Receiver Pairs

An improvement on the DRP configuration can be realized by adding a second transmitter to achieve symmetric source and receiver pairs. For the purposes of the present discussion, this configuration is denoted "SSRP". The SSRP configuration is an improvement on the DRP configuration as it further removes approximations associated with measuring an operating condition, such as wafer temperature. The maing advantage of the SSRP configuration is that it accurately removes characteristics of the transmitters and receivers from the measurement of wafer characteristics. The main disadvantage is its use of an additional pin (or two, compared to the SET configuration) to achieve the same end.

Referring to FIGS. 20A and 20B, there are illustrated the two operations that are needed in the preferred embodiment to perform an SSRP measurement. Each of these operations is essentially the same as a DRP operation, described in reference to FIG. 19. The operations are made in sequence in no particular order and are separated in time so that the resulting signals are not superimposed. In both FIGS. 20A and 20B the transducers 21 and 29 are sourcing transducer pins and the transducers 24 and 27 are receiving transducer pins. In the first operation (FIG. 20A) a wave 22 excited in the sourcing pin 21 excites a Lamb wave in the wafer 1 in the manner previously described that is received at both the receiving pins 25 and 27. The path of the Lamb wave includes a subpath 23 between the sourcing pin 21 and the first receiving pin 24 and a subpath 26 between the receiving pin 25 and the receiving pin 27. The Lamb wave is coupled into the receiving pins 24, 27 as respective waves 25 and 28, which are received at respective transducers, which generate two corresponding signals T2(t) and T3(t).

The second operation (FIG. 20B) is similar to the first operation (FIG. 20A) but involves exciting a wave 30 in the second sourcing pin 29 that is coupled into the wafer 1 as a second Lamb wave. The second Lamb wave propagates over the subpaths 31 and 33 and is coupled into the receiving pins 24 and 27 and received at respective transducers, which generate two corresponding signals T4(t) and T5(t). The four signals T2(t), T3(t), T4(t) and T5(t) are processed in a way that amounts to averaging the measurements derived from the independent DRP operations. This enables any differences between the receiving pins 24 and 27 to cancel in light of differences between the measurements of the presumably identical operating condition that exists between the pins 24, 27 from Lamb waves excited by the different transmitting pins 21, 29. Aspects of the SSRP measurement that differ from the individual DRP case are now described.

The spectra of the waveform T4(t) is given by the expression $W_{T4} = \eta_0 \eta_4 \eta_3 \exp(i(\phi_{p4} + \phi_{p3} + \phi_{D4})) \xi_{4L} \xi_{L3} \xi_4$, where $\phi_{D4}$ is the phase of a plane Lamb wave propagating directly from the sourcing point 29 to the receiving pin 27 and $\zeta_4$ is a corresponding diffraction correction factor. The subscript 4 in this expression indicates quantities associated with the path between the receiving transducer 27 and the sourcing transducer 29. Recall that the sub-script 3 is associated with the receiving transducer 27 and the sourcing transducer 21.

The second receiving transducer 24 detects the expanding circular Lamb wave after it has propagated an additional distance along the path 33, with the resulting spectrum: $W_{T5} = \eta_0 \eta_4 \eta_2 \exp(i(\phi_{p4} + \phi_{p2} + \phi_{D5})) \xi_{4L} \xi_{L2} \zeta_5$, where $\phi_{D5}$ is the phase of a plane Lamb wave propagating directly from the sourcing point 29 to the receiving pin 24 and $\zeta_5$ is a corresponding diffraction correction. The subscript 5 in this expression indicates quantities associated with the receiving transducer 24 and the sourcing transducer 29. Recall that the subscript 2 is associated with the receiving transducer 24, subscript 3 with the receiving transducer 27, subscript 1 with the source transducer 21 and subscript 4 with the source transducer 29.

The desired phase perturbation in light of the four signals is given by Eq. (13).

$$\Delta[(\angle W_{T3} - \angle W_{T2}) + (\angle W_{T5} - \angle W_{T4})] \approx \Delta[\phi_{D3} - \phi_{D2} + \phi_{D5} - \phi_{D4}] \quad \text{Eq. (13)}$$

That is, the sum of the differences in the angle of the related spectra should be the same as the corresponding sum of differences of the phases measured at the pins 24 and 27 due to Lamb waves excited at the pins 21 and 29. In the SSRP configuration, the only approximations underlying the phase perturbation expression is that $\Delta[\angle \zeta_3 - \angle \zeta_2 + \angle \zeta_5 - \angle \zeta_4] = 0$; i.e., that diffraction can be neglected. Thus, the SSRP geometry inherently removes all undesirable effects of the pins ($\phi$ and $\eta$) and the contacts ($\psi$ and $\xi$) that are factors in the other configurations. In most cases, the diffraction effects that are still present are vanishingly small; even these can be accounted for theoretically, if necessary.

A significant advantage of the SSRP configuration is that it can be used to calculate absolute rather than relative velocities. This is made possiblb by removing the $\Delta$ in Eq. (13), which yields the following result:

$$(\angle W_{T3} - \angle W_{T2}) + (\angle W_{T5} - \angle W_{T4}) \approx \phi_{D3} - \phi_{D2} + \phi_{D5} - \phi_{D4} = 4\pi f D_6 / v.$$

In this expression $D_6 = D_3 - D_2 = D_5 - D_4$ is the distance between the receiver pins.

The primary reason for employing the $\Delta$ (i.e., differences from a setup condition) above is to approximately remove the characteristics of the transducers fl via the approximation in Eq. (3). The SSRP configuration removes all $\eta$'s without the need for the $\Delta$. As a result, it is possible with the SSRP configuration to accurately calculate absolute results without setup values, whereas this is not possible in the other configurations.

Ideally, the pins 21, 24, 27 and 29 are in a line. Other geometries are also workable with similar results. The SSRP geometry is as insensitive to nonlinearity as the differential receiver pair. More than two receivers (or transmitters) can be used to improve the signal-to-noise ratio and resolve phase ambiguities for long differential paths $D_6$ in the DRP DSP and SSRP geometries.

The preferred embodiments described so far presume that measurements are made on a wafer with a specific, known orientation with respect to the pins. Alternative embodiments are now described wherein the wafer can have different orientations with respect to the pins.

G. Silicon Anisotropy

Because silicon is a cubic crystal, the velocities of elastic waves, including Lamb waves, in silicon are anisotropic, i.e., the velocities are a function of the direction of propagation. In particular, the velocities of Lamb waves propagating at various angles on a plate of silicon whose faces are normal to the [1 0 0] direction (i.e., the crystallographic [1 0 0] coordinate direction) exhibit fourfold symmetry, as shown in FIG. 23A.

Referring to FIG. 23A, there is shown a plot of phase velocity versus propagation angle (i.e., velocity anisotropy) of the zeroth-order antisymmetric Lamb wave on a [1 0 0], 725 $\mu$m-thick silicon plate at 500 kHz for two temperatures (20 C and 400 C). The difference between the two curves in FIG. 23A is proportional to the thermal-acoustic coefficient $\partial v / \partial T$, which is the basis for acoustic thermometry. Referring to FIG. 23B, there is shown a plot of the relative variation of the thermal-acoustic coefficient versus propagation angle about its angular mean for the system for which velocity anisotropy is displayed in FIG. 23A. In spite of the rather large variation in the velocity itself of about 2%, the thermal-acoustic coefficient is nearly isotropic, with peak-o-peak variations of less than 0.1%, as shown in FIG. 23B. In these and subsequent figures zero degree propagation corresponds to propagation along the [0 1 0] axis.

Given this velocity anisotropy, if the direction of propagation is unknown, e.g., if the wafer rotates by some arbitrary amount between wafer-by-wafer calibration and temperature measurement, the velocity anisotropy illustrated in FIG. 23A can produce a large error in the measured temperature, as shown in FIG. 24.

Referring to FIG. 24, there is shown a plot of the error (apparent temperature variation) in measured temperature due to assuming that the measurement was made in the [0 1 0] direction when it was actually made at some other wafer orientation. The error is symmetrical about 45 degrees and repeats every 90 degrees. Therefore, only relative orientations between 0 and 45 degrees are shown in FIG. 24. Six curves are plotted corresponding to different combinations of the three wafer thicknesses (706.875 $\mu$m, 725 $\mu$m, 743.125 $\mu$m) and two wafer temperatures (20 C, 400 C) listed in the legend. At this scale the curves appear to be practically identical, indicating that the temperature error is highly dependent on relative wafer orientation and relatively insensitive to differences in temperature and/or wafer thickness.

One method of reducing this error is to independently measure the orientation of the wafer with respect to the propagation direction, and then to theoretically correct the measured temperature. The difficulty of this approach is that the slope of the error with respect to angle (as illustrated in FIG. 24) is quite large, so that a small error in determining the orientation, e.g., 1 degree, can lead to errors in temperature as large as 100 C.

There are two acoustic means of reducing the error due to orientation uncertainty in acoustic thermometry that can be used either independently or together. Both measurement error reduction techniques involve making measurements at least two propagation directions on the wafer. In the first method two measurements with 45 degrees±n*90 degrees (where n is an integer) between their orientations are averaged. In the second method, multiple measurements at orientations differing by a known amount determine the orientation of the wafer, which is then used to theoretically correct the acoustic thermometer.

Referring to FIG. 25, there is shown a preferred embodiment for implementing the first error correction technique described in reference to FIG. 24. This embodiment includes three pins 420, 422, 424 whose tips are in contact with a wafer 426. A direct path 428 between the pin 420 and the pin 422 differs by an unknown angle φ from the [0 1 0]. The angle Δφ between the direct path 428 and the direct path 430 between the pin 420 and the pin 424 is 45 degrees±n*90 degrees. The average acoustic temperature ($T_{avg}$) resulting from the two measurements can be represented as $T_{avg}$= ($T_φ$+$T_{φ+45}$)/2, where $T_φ$ represents the temperature measured along the path 428 and $T_{φ+45}$ represents the temperature measures along the path 430. As described above, a measurement error results if it is assumed that φ is zero but φ actually has another value. The measurement error in $T_{avg}$ is shown in FIG. 26, which is plotted in the same manner as FIG. 24 for the case where the path 428 is assumed to be in the [0 1 0] direction but is at some other wafer orientation. Note that the error in $T_{avg}$ is far smaller than the error resulting from a single measurement (FIG. 24). This method can also be used with other anisotropy symmetries, with minor modifications. E.g., for a silicon wafer whose surface is normal to the [111] direction, the angular dependencies on the surface repeat every 120 degrees, so the angle Δφ must be 60 degrees.

The second acoustic approach to reducing the effect of anisotropy on the acoustic thermometer is to measure the orientation of the wafer acoustically. This approach is also described in reference to FIG. 25. Respective measurements are made for the two paths 428, 430, which are radially separated by an angle Δφ that is not a multiple of 90 degrees and optimally is 45 degrees±n*90 degrees. The temperature of the wafer 426 must be homogeneous and the wafer's thickness (i.e., flexural stiffness) must be homogeneous but need not be isotropic. When Δφ is 45=degrees the ratio between the measurements made for the paths 428, 430 is a function of the angle φ between the [0 1 0] direction and the path 428 (FIG. 25). As seen in FIG. 26, which is a plot of the ratios of path 428, 430 velocities for Δφ and φ=45 degrees, the ratio is not a strong function of the temperature or thickness of the wafer (i.e., the six curves are practically identical). As a result essentially one value of the ratio can be used for all operating conditions (e.g., thicknesses and temperatures). The relation between φ and the ratio is one-to-one over a 45 degree range of φ, and thus can be inverted unambiguously over that range. That is, the angle φ can be derived by inverting the ratio of the two measurements computed for the paths 428, 430.

FIG. 27 is a plot of the error in the inverted angle versus relative wafer orientation for the six exemplary operating conditions. The inversion in general does not know about the thickness or the temperature of the wafer and so must be based on single relationship between ratio and angle. In the preferred embodiment this relationship is established for the operating condition whose ratio exhibits the greatest variation over angle, i.e., for the higher temperature of the thinnest wafer. If φ is not constrained to a 45 degree range there is an eightfold ambiguity in inverting ratio for angle, expressed as follows: φ=±φ$_r$+n×90°, where φ is the absolute orientation of the wafer and φ$_r$ is the phase increment determined from the ratio of velocities. This ambiguity is not a problem if the orientation is being used to correct ultrasonic temperature, which has the same angular symmetry, as discussed below in reference to FIG. 29.

Once the angle φ of the wafer is known, the temperature can be corrected. The correction is simply the negative of the error described in reference to FIG. 24. However, since the temperature and thickness are unknown, a single value must be used, whereas six are shown in the figure. A reasonable choice is the mean of the six. The remaining error after correcting for the rotation with the inverted angle and mean error is shown in FIG. 29, which is a plot of apparent temperature as a function of relative wafer orientation. Note that these errors are substantially reduced from the uncorrected errors shown in FIG. 24. The remaining error has two sources. The first source is the error in angle inversion due to the lack of knowledge about temperature and thickness in that procedure. Fortunately, this error is very small where the correction is very sensitive to angle, i.e., at 22.5 degrees, and its error is largest were the correction is not very sensitive to angle, i.e., at 0 and 90 degrees. The second source of error is the uncertainty in the amount of correction due again to lack of knowledge of thickness and temperature. Various iterative or nonlinear-inversion methods or additional information about temperature or thickness could further reduce the errors. Also, constraining the operating range (thickness and temperature) will reduce the error.

The two methods described above for desensitizing the acoustic thermometer to uncertainties of wafer orientation can be used simultaneously. For example, the average temperature is first calculated using the first method (i.e., by averaging two temperature measurements made at Δφ=45 degrees). Then, using the second method, the orientation φ of the wafer is computed by inverting the ratio of the measurements. An orientation-dependent correction for the average temperature is then calculated as, e.g., the mean of the curves in FIG. 26. Finally, the correction for the inverted angle is subtracted from the average temperature. Referring to FIG. 30, there is shown a plot of the error (i.e., apparent temperature variation) in the resulting temperature measurement. Note that this result has lower error (within ±1.5 C) than the average temperature produced by the first method alone or the corrected (single) temperature.

The acoustic method for determining the orientation of the wafer may be useful for applications other than correcting acoustic thermometry. However, the angular ambiguity may be a problem. With the ratio of two measurements, the ambiguity of orientation can be eliminated if the initial orientation of the wafer is known to ±22.5 degrees, e.g., to be between 0 and 45 degrees. By adding a third measurement, it is possible to reduce the eightfold ambiguity to fourfold, so that knowing the initial orientation to ±45 degrees is sufficient. Further reductions in ambiguity are not possible due to the inherent fourfold symmetry of single-crystal silicon cut perpendicular to the [100] direction. Again, there are obvious differences for anisotropic substrates with different symmetries.

Characteristics of the zeroth-order antisymmetric Lamb wave (also called the A0 mode) are well known and are described at depth in prior art literature. Due to these characteristics the A0 mode Lamb wave is a desirable candidate for the Lamb waves excited by the embodiments disclosed herein. The U.S. Pat. No. 5,469,742 ("Acoustic Temperature and Film Thickness Monitor and Method") over which the present invention defines improvements describes how A0 Lamb waves and other Lamb wave modes (symmetric and antisymmetric) can be excited in test objects, such as semiconductor wafers. These prior art teachings are entirely incorporated herein by reference. Note that any Lamb wave mode can be employed by the present invention as long as it has velocity characteristics that vary as a function of temperature or some other desired operating condition and has transmission characteristics that can be measured using the described measurement techniques. In addition, other acoustic waves, such as Raleigh waves, compressional waves, etc. can also be employed.

H. Temperature from an Echo

As stated above, the delay of the echo signal depends on the temperature of the pin, which itself is influenced by the temperature of the wafer. Under some conditions, this could be a suitable temperature measurement: if the wafer temperature changes slowly, and changes in the pin temperature are due only to changes in wafer temperature. These requirements are overly restrictive for many applications.

An improved approach to measuring temperature from an echo signal, to remove the requirements mentioned above, is illustrated in FIG. 21. The key change is the addition of a resonator 86 to the pin structure, additionally consisting of a pin 83 and a piezoelectric element 82. The resonator 86 is formed by introducing an acoustic discontinuity along the length of the pin. FIG. 22 shows several types of resonators that can be employed in the present invention. This method is different from those in the prior art that use quartz resonators: in that the piezoelectric material and attendant electrical connections of the present invention are remote from the location of temperature sensitivity.

In FIG. 22A, the resonator is produced by a cut that has been made in the pin. In FIG. 22B, it is a different material bonded to the end of the pin. In FIG. 22C it is a ball bonded to the end of the pin. In FIG. 22D it is a section of the pin with a different cross-section. In FIG. 22E, the resonator is a structure held in contact with the pin without bonding and in FIG. 22F the resonator is a flexural member attached to the tip of the pin. These embodiments are only illustrative of the many possibilities.

The introduction of an additional boundary (i.e., a resonator) causes resonances at the tip of pin. These resonances trap acoustic energy and reradiate it at a later time. The resonances are typically characterized by a frequency f and a quality factor Q. The frequency f, or its inverse, the period, $t_r = 1/f$, is of primary importance here, since it is determined by the scale of the resonator I and the appropriate velocity of sound in the resonator v as $f = \psi/v$, where $\psi$ is a constant depending on the exact resonance of interest. Since the scale and the velocity are weak functions of temperature, a measurement of f can yield a measurement of temperature $T = T_0 + \alpha(f - f_0)$, where $T_0$ and $f_0$ are the temperature and resonant frequency under some setup conditions, and a is a calibration factor. More generally, T can be considered a more complex function of f, e.g., with memory and/or nonlinearity. The frequency of the resonance can be determined by spectral estimation, for example from the phase spectrum or the group-delay spectrum, both of which techniques are known in the art. Similarly, the resonance frequency could be determined from a measurement of the resonant period, $t_0$.

There are at least three advantages of introducing the resonator 86. Measuring the frequency of the resonator localizes the measurement of temperature to the resonator. Without the resonator, the echo delay is an indication of the average temperature of the whole pin. The average over the whole pin responds slowly to temperature changes of the wafer because time is required to diffuse the heat over the length of the pin. Thus, a first advantage of measuring resonator frequency as opposed to echo transit time is that the former measurement is more responsive to temperature changes than the latter. The pre-existing temperature of the whole pin affects the effect of the wafer's temperature on the pin's temperature. The temperature of those portions of the pin further from the wafer can be influenced more by the temperature of objects other than the wafer. As a result, a second advantage obtained from using a resonator is that localization of the acoustic measurement of temperature via resonator frequency is more completely controlled by the temperature of the wafer than is the case for an echo transit time measurement. Finally, if the boundary lowers the thermal conduction between the pin tip and the rest of the pin, it will cause thermal energy to be trapped in the resonator, so that it will more closely track the temperature of the wafer than the average temperature of the whole pin. This third advantage can be enhanced by using a material of high thermal conductivity for the resonator, a material of low thermal conductivity for the pin, and by minimizing the thermal conductivity of the contact between the resonator and the pin.

The quality of the resonator measurement is affected by the amount of energy that enters the resonator, and the rate at which it re-radiates. Both factors are affected by the acoustic contact between the pin and the resonator. The transmission coefficient for acoustic energy at this contact must be large enough to let energy into the resonator, and low enough to allow the energy in the resonator to resonate, i.e., to give a sufficiently high Q. The thermal conductivity at this juncture and the acoustic transmission coefficient are likely to be correlated.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

For example, while the preferred embodiments described herein are directed to pin transducers, the teachings of the present invention can be implemented using any combination of sources and receivers that are able, respectively, to excite and detect acoustic waves in a target object (such as a wafer). A good candidate for the source (corresponding to a piezoelectric transducer and pin) is a laser that generates a beam directed to an excitation point on the target object where the acoustic waves are to be excited. In this alternative embodiment, heating of the target at the excitation point excites the desired acoustic waves. Good candidates for the receiver (corresponding to the piezo-electric transducer and pin) include laser detectors consisting of either a knife edge or an interferometer that measures deflection of the target object at a defection point caused by arrival of acoustic waves thereat. Another example of a modification would be to use amplitude or attenuation coefficient as a measurement. This would be consistent with interpreting velocity generally as complex velocity, as is known in the art.

What is claimed is:

1. An improved apparatus for characterizing a substrate, comprising:
    a plurality of pin transducers, each having a probe end configured to couple acoustic energy between the pin transducer and the substrate and a transducer end configured to convert the acoustic energy in the pin transducer to external electrical signals and vice-versa;
    a first set of the pin transducers including a transmitting pin configured so that the transducer end of the transmitting pin when coupled to a signal pulse of a predetermined character, excites pin acoustic waves in the pin that the probe end of the transmitting pin couples into the substrate as substrate acoustic waves;

a second set of the pin transducers including one or more receiving pins configured so that the transducer end of a respective receiving pin produces a transmitted electrical signal representing the acoustic energy in a transmitted wave coupled from the substrate to the respective pin by that pin's probe end in response to arrival at that probe end of the substrate acoustic waves; and acquisition and processing modules configured to perform a characterization measurement wherein:

the acquisition module is configured to (1) receive the transmitted electrical signal during a measuring period following the signal pulse; and (2) digitize the received transmitted signals; and the processing module is configured to (3) digitally compute from the digitized, received transmitted signals a respective measurement set correlated to spectral frequency components of the substrate acoustic waves.

2. The apparatus of claim 1, wherein the first set and second set have a configuration that is at least one of:

(a) the first set of pin transducers includes exactly one transmitting pin and the second set of pin transducers includes exactly one receiving pin;

(b) the first set of pin transducers includes exactly one transmitting pin and the second set of pin transducers includes at least two receiving pins;

(c) the probe ends of the transmitting pins and the receiving pins are arranged diametrically with respect to the surface of the substrate;

(d) the probe ends of the transmitting pins and the receiving pins are collinear;

(e) the first set of pin transducers includes two transmitting pins and the second set of pin transducers includes two receiving pins; and (f) at least one of the pin transducers belongs to both of the sets.

3. The apparatus of claim 2, wherein the acquisition module is configured to excite and accept measurements from the pin transducers associated with one or more processing stations; each processing station being capable of performing a set of process steps on a respective substrate;

a plurality of the processing stations compose a processing cluster; and the processing module is coupled to the acquisition module to control third measurements made by the acquisition module in relation to process steps ongoing in the corresponding processing stations and to derive from the measurements a process measurement set for the respective substrate, the apparatus thereby being capable of simultaneously characterizing one or more substrates being processed in the cluster.

4. The apparatus of claim 3, wherein the substrates are rotated among at least a subset of the processing stations within the processing cluster for completion of different processing steps;

the cluster includes a calibration station at which each of the substrates can be maintained in such a condition that calibration values of at least one substrate characteristic are known for that substrate, each of the substrates being rotated to the calibration station before the commencement of one or more of the processing steps;

the calibration station is coupled to the acquisition and processing modules, which direct the calibration station to compute a calibration measurement set corresponding to the calibration values and determine independently propagation characteristics for that substrate relating the calibration measurement set to the calibration values; and the processing module stores propagation characteristics for each of the substrates so that data can be provided to the processing module as needed to compute process values of at least one substrate characteristic for the corresponding substrate.

5. The apparatus of claim 1, wherein the measurement set comprises quantities computed from respective phases of one or more spectral components of a frequency spectrum for the transmitted electrical signal.

6. The apparatus of claim 1, wherein the measurement set comprises quantities computed from respective times of arrival of one or more spectral components of a frequency spectrum for the transmitted electrical signal.

7. The apparatus of claim 1, wherein the measurement set comprises an inverse square velocity for one or more spectral components of a frequency spectrum for the transmitted electrical signal.

8. The apparatus of claim 1, wherein:

at least one of the receiving pins is further configured to produce an echo electrical signal; and the acquisition module is further configured to (1) receive the echo electrical signals during a measuring period following the signal pulse; and (2) digitize the received echo signals.

9. The apparatus of claim 8, wherein the measurement set comprises quantities computed from respective phases of one or more spectral components of frequency spectra for the transmitted and echo signals.

10. The apparatus of claim 8, wherein the measurement set comprises quantities computed from respective times of arrival of one or more spectral components of frequency spectra for the transmitted and echo signals.

11. An improved apparatus for characterizing a substrate, comprising:

a first set of one or more source transducers configured to excite acoustic waves in the substrate at corresponding excitation points;

a second set of at least two receiving transducers, each being configured to detect acoustic waves in the substrate and to produce a transmitted electrical signal representing acoustic energy in the substrate at a probe point due to the excited acoustic waves;

acquisition and processing modules configured to perform a characterization measurement, wherein the acquisition module is configured to receive the transmitted electrical signals during at least one measuring period following the excitation of the acoustic waves, and the processing module is configured to compute from the transmitted electrical signals a measurement set correlated to spectral frequency components of the acoustic waves between at least a subset of the probe points; and the acquisition and processing modules are configured to compute at least one unknown substrate characteristic associated with at least the orientation of the substrate existing at a process time based on the measurement set computed at the process time for the at least one source transducer and the at least two receiving transducers.

12. The apparatus of claim 11, wherein the processing module includes:
(a) a setup database storing information about the at least one characteristic for a setup substrate at a setup time and the corresponding measurement set;
(b) a characteristics database representing independent in-substrate characteristics dependencies of the acoustic waves on the at least one characteristic; and
the processing module is configured to compute one set of process values of the at least one characteristic between the subset of probe points for the process time based on the corresponding measurement set and information in the databases.

13. The apparatus of claim 12, wherein the propagation database is selected from the set consisting of:
propagation data generated for the substrate being characterized; and
propagation data generated for other substrates with compositions similar to that of the substrate.

14. The apparatus of claim 12, wherein the setup time is selected from the set consisting of:
one or more times during processing when at least one of the characteristics is known; and
one or more times preceding processing when at least one of the characteristics is known.

15. The apparatus of claim 11, wherein one other characteristic is measured, including at least one of substrate temperature;
substrate thickness;
thickness of a film on the substrate; and
state of the film.

16. An improved apparatus for characterizing a substrate, comprising:
a first set of one or more source pin transducers configured to excite acoustic waves in the substrate at corresponding excitation points;
a second set of one or more receiving pin transducers, each being configured to detect acoustic waves in the substrate and to produce a transmitted electrical signal representing acoustic energy in the substrate at a probe point due to the excited acoustic waves;
at least one of the receiving pin transducers being further configured to produce an echo electrical signal; and
acquisition and processing modules configured to perform a characterization measurement, wherein the acquisition module is configured to receive the transmitted and echo electrical signals during a measuring period following the excitation of the acoustic waves, and the processing module is configured to compute from the transmitted and echo electrical signals a measurement set correlated to spectral frequency components of the acoustic waves between at least a subset of the points.

17. The apparatus of claim 16, wherein the first set and second set have a configuration that is at least one of:
(a) the first set includes exactly one source pin transducer and the second set includes exactly one receiving pin transducer;
(b) the first set includes exactly one source pin transducer and the second set includes at least two receiving pin transducers;
(c) the source pin transducers and the receiving pin transducers are configured such that the excitation and probe points are arranged diametrically with respect to the surface of the substrate;
(d) the probe points and the excitation points are collinear;
(e) the first set includes two source pin transducers and the second set includes two receiving pin transducers; and
(f) at least one of the pin transducers belongs to both of the sets.

18. The apparatus of claim 16, wherein
the acquisition and processing modules are further configured to compute a plurality of process measurement sets by performing the characterization measurement on the substrate at a process time during semiconductor processing wherein at least one characteristic associated with the substrate is unknown;
the acquisition and processing modules are further configured to compute a plurality of setup measurement sets by performing the characterization measurements on a similar substrate at a setup time wherein the at least one characteristic is known; and
the processing module being configured to compute one set of process values of the at least one characteristic at the process time between the at least one pin transducer configured to produce an echo electrical signal and at least one other of the transducers based on the corresponding setup and process measurement sets and information representing independent in-substrate of the acoustic waves on the at least one characteristic.

19. The apparatus of claim 18, wherein the processing module includes:
(a) a setup database storing information about the at least one characteristic of a setup wafer at the setup time and a corresponding setup measurement set; and
(b) a propagation database representing independent in-substrate propagation dependencies of the acoustic waves on the at least one characteristic.

20. The apparatus of claim 19, wherein the propagation database is selected from the set consisting of:
propagation data generated for the substrate being characterized; and
propagation data generated for other substrates with compositions similar to that of the substrate.

21. The apparatus of claim 18, wherein:
the setup time is selected from the set consisting of
one or more times during processing when at least one of the characteristics is known; and
one or more times preceding processing when at least one of the characteristics is known.

22. The apparatus of claim 18, wherein the at least one characteristic being measured is at least one of:
substrate temperature;
substrate thickness;
thickness of a film on the substrate; and
state of the film.

* * * * *